United States Patent [19]

Kozlik et al.

[11] Patent Number: 4,629,727
[45] Date of Patent: Dec. 16, 1986

[54] THERAPEUTIC AGENTS

[75] Inventors: Antonin Kozlik, Clifton; Wilfred H. Wells, Radcliffe-on-Trent, both of England

[73] Assignee: The Boots Company PLC, England

[21] Appl. No.: 536,669

[22] Filed: Sep. 28, 1983

[30] Foreign Application Priority Data

Sep. 30, 1982 [GB] United Kingdom ............... 8227898
Sep. 30, 1982 [GB] United Kingdom ............... 8227901

[51] Int. Cl.⁴ .................. A61K 31/135; C07C 87/455
[52] U.S. Cl. .................................. 514/237; 548/561;
549/74; 514/222; 549/492; 560/38; 514/247;
560/250; 564/164; 514/255; 564/220; 514/256;
564/305; 514/331; 564/440; 564/442; 514/357;
564/443; 558/426; 514/365; 514/378; 514/381;
514/383; 514/400; 514/406; 514/427; 514/438;
514/471; 514/651; 514/654; 544/59; 544/162;
544/224; 544/335; 544/336; 546/246; 546/329;
548/146; 548/205; 548/247; 548/254; 548/255;
548/262; 548/342; 548/378
[58] Field of Search ............... 544/336, 335, 224, 162,
544/59; 546/329, 246; 549/492, 74; 548/561,
342, 378, 262, 255, 254, 205, 146, 247; 560/38,
250; 564/305, 440, 443, 442, 164, 220; 514/654,
651, 471, 438, 427, 357, 331, 400, 406, 255, 256,
247, 383, 381, 365, 378, 237, 222

[56] References Cited

U.S. PATENT DOCUMENTS 4,443,449 4/1984 Jeffery .................................. 424/250
4,522,828 6/1985 Jeffery et al. ........................ 514/646

FOREIGN PATENT DOCUMENTS 3212682 10/1982 Fed. Rep. of Germany ...... 424/250
973887 10/1964 United Kingdom .
1530172 12/1979 United Kingdom .

OTHER PUBLICATIONS

V. P. Arya and S. J. Shenoy, Synthesis of New Heterocycles: Part XV–Synthesis of Novel Cyclic and Acyclic Sulphamides, Indian Journ. of Chem., vol. 14B, pp. 766–769 (1976); Chem. Abs. 87 23236s.
A. L. Mndzhoyan, et al., Substituted Acetic Acids XXXII, Aminoesters of 1-(Alpha–Naphthyl) Cycloalkane-1-Carboxylic Acids and 1-(Alpha-Naphthyl) Cycloalkane-1-Methyl Guanidines, Armyanskii Khimi-chesdii Zhurnal, vol. 29, No. 2, pp. 194–199 (1976); Chem. Abs. 85 32678y; translation included.
A. Kalir, et al., 1-Phenylcycloalkylamine Derivatives, Israel J. Chem. 5(5), pp. 223–229 (1967).

Primary Examiner—Robert Gerstl
Attorney, Agent, or Firm—Jacobs & Jacobs

[57] ABSTRACT

Compounds of formula I

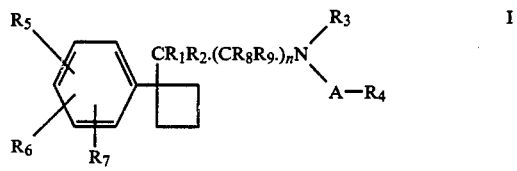

in which n=0 or 1;
in which, when n=0, $R_1$ is H, an alkyl, a cycloalkyl, a cycloalkylmethyl, an alkenyl or, an alkynyl group a heterocyclic ring or an optionally substituted phenyl ring or when n=1, $R_1$ is H or an alkyl group;
in which $R_2$ and $R_3$ are H or an alkyl group;
in which A is a group of formula III

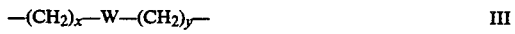

$$-(CH_2)_x-W-(CH_2)_y-\qquad\text{III}$$

in which W is an oxygen atom or a group of formula $-S(O)_m-$, a group of formula $-CR_{12}R_{13}-$, a cycloalkylidene group or a cycloalkylene group; x is 0 or an integer from 1 to 5; y is 0 or an integer from 1 to 5.
in which $R_4$ is a carbocyclic ring, a heterocyclic ring, a cyano group, a carbamoyl group, an alkoxycarbonyl group, an amido group, an acyloxy group, a hydroxy group, a thiol group, or a group of formula $-OR_{20}$, $-SR_{20}$, $-SOR_{20}$ or $SO_2R_{20}$.
in which $R_5$, $R_6$ and $R_7$ are H, halo, trifluoromethyl, hydroxy, an alkyl group, an alkoxy or alkylthio group, phenyl or $R_5$ and $R_6$, together with the carbon atoms to which they are attached, form an optionally substituted second benzene ring;
in which $R_8$ and $R_9$ are H or an alkyl group containing 1 to 3 carbon atoms;
and pharmaceutically acceptable salts thereof have utility in the treatment of depression. Processes for their preparation and compositions containing them are disclosed.

40 Claims, No Drawings

THERAPEUTIC AGENTS

This invention relates to compounds having useful therapeutic activity particularly but not exclusively as antidepressants, to pharmaceutical compositions containing such compounds and to processes for the preparation of such compounds.

The present invention provides compounds of formula I

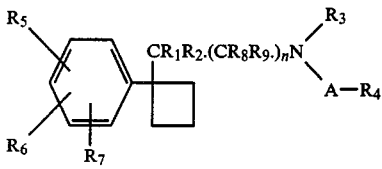

in which n=0 or 1;

in which, when n=0, $R_1$ is H, a straight or branched chain alkyl group containing 1 to 6 carbon atoms, a cycloalkyl group containing 3 to 7 carbon atoms, a cycloalkylmethyl group in which the cycloalkyl group contains 3 to 7 carbon atoms, an alkenyl group containing 3 to 6 carbon atoms, an alkynyl group containing 3 to 6 carbon atoms, a heterocyclic ring containing one or more heteroatoms selected from N, O and S or a group of formula II;

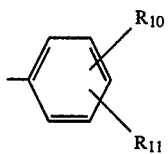

in which, when n=1, $R_1$ is H or an alkyl group containing 1 to 3 carbon atoms;

in which $R_2$ is H or an alkyl group containing 1 to 3 carbon atoms;

in which $R_3$ is H or a straight or branched chain alkyl group;

in which A is a group of formula III

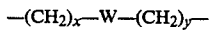

in which W is an oxygen atom or a group of formula $—S(O)_m—$ in which m is 0, 1 or 2, a group of formula $—CR_{12}R_{13}—$, a cycloalkylidene group containing 3 to 6 carbon atoms or a cycloalkylene group containing 3 to 6 carbon atoms; x is 0 or an integer from 1 to 5; y is 0 or an integer from 1 to 5 (with the proviso that when W is an oxygen atom or a group of formula $S(O)_m$, x and y are both integers from 1 to 5); $R_{12}$ and $R_{13}$ which are the same or different are H, an alkyl group containing 1 to 3 carbon atoms, hydroxy, methoxy or benzyl;

in which $R_4$ is a carbocyclic ring, a heterocyclic ring containing one or more heteroatoms selected from N, O and S, a cyano group, a carbamoyl group of formula $—CONR_{14}R_{15}$ in which $R_{14}$ and $R_{15}$ which are the same or different are H, an alkyl group containing 1 to 3 carbon atoms or $R_{14}$ and $R_{15}$ together with the nitrogen to which they are attached form a heterocyclic ring, an alkoxycarbonyl group of formula $—COOR_{16}$ in which $R_{16}$ is an alkyl group containing 1 to 3 carbon atoms, an amido group of formula $—N(R_{17})COR_{18}$ in which $R_{17}$ and $R_{18}$, which may be the same or different, are alkyl groups containing 1 to 4 carbon atoms or $R_{17}$ and $R_{18}$ together with the nitrogen atom and carbonyl group to which they are attached form a ring, an acyloxy group of formula $—OCOR_{19}—$ in which $R_{19}$ is an alkyl group containing 1 to 3 carbon atoms, a hydroxy group, a thiol group, or a group of formula $—OR_{20}$, $—SR_{20}$, $—SOR_{20}$ or $SO_2R_{20}$ in which $R_{20}$ is a straight or branched chain alkyl group containing 1 to 4 carbon atoms or an optionally substituted phenyl group;

in which $R_5$, $R_6$ and $R_7$ which are the same or different, are H, halo, trifluoromethyl, hydroxy, an alkyl group, and alkoxy or alkylthio group, phenyl or $R_5$ and $R_6$, together with the carbon atoms to which they are attached, form an optionally substituted second benzene ring;

in which $R_8$ and $R_9$, which are the same or different, are H or an alkyl group containing 1 to 3 carbon atoms;

in which $R_{10}$ and $R_{11}$, which are the same or different, are H, halo, an alkyl group containing 1 to 3 carbon atoms or an alkoxy group containing 1 to 3 carbon atoms;

and pharmaceutically acceptable salts thereof.

When n=0 and $R_1$ is an alkyl group the alkyl group contains 1 to 6 carbon atoms (for example methyl, ethyl, propyl, isopropyl, isobutyl, or branched hexyl). When $R_1$ is a cycloalkyl group the cycloalkyl ring contains 3 to 7 carbon atoms (for example cyclopropyl, cyclobutyl, cyclopentyl or cyclohexyl). When $R_1$ is a cycloalkylmethyl group the cycloalkyl ring contains 3 to 6 carbon atoms (for example cyclopropyl, cyclobutyl, cyclopentyl or cyclohexyl). When $R_1$ is an alkenyl or alkynyl group, the group contains 3 to 6 carbon atoms (for example allyl or propynyl).

When $R_1$ is a heterocyclic ring, the ring may contain 5 or 6 atoms and may contain one heteroatom (for example furyl, thienyl, pyrrolyl, pyridyl, tetrahydrofuryl or tetrahydrothienyl) or more than one heteroatom which may be the same (for example imidazolyl, pyrazolyl, pyrazinyl, pyrimidinyl, pyridazinyl, triazolyl, tetrazolyl or dithianyl) or different (for example thiazolyl). The heterocyclic ring may be substituted for example by one or more alkyl groups (for example methyl), halo (for example fluoro or chloro), hydroxy, alkoxy groups (for example methoxy) or trifluoromethyl. In preferred compounds of formula I, $R_1$ is a furyl, thienyl, pyridyl, tetrahydrofuryl, dithianyl, methylfuryl, methylpyrrolyl, methylimidazolyl, methylpyrazolyl, methyltetrazolyl or methylthiazolyl group.

When $R_1$ is a group of formula II $R_{10}$ and/or $R_{11}$ may be H, fluoro, chloro, bromo, an alkyl group containing 1 to 3 carbon atoms (for example methyl) or an alkoxy group containing 1 to 3 carbon atoms (for example methoxy).

When n=1 and $R_1$ is an alkyl group the alkyl group contains 1 to 3 carbon atoms (for example methyl).

When $R_2$ is an alkyl group it contains 1 to 3 carbon atoms (for example methyl).

When $R_3$ is alkyl, the alkyl group contains 1 to 4 carbon atoms (for example methyl, ethyl or propyl).

When the group W is a cycloalkylene or cycloalkylidene group, the group may be cyclohexylene or cyclohexylidene.

When the group $R_4$ is a carbocyclic ring, the ring may contain 3 to 7 carbon atoms (for example cyclohexyl) and the ring may contain one or more double bonds (for example cycloheptenyl) or the ring may be phenyl optionally substituted by halo (for example fluoro or chloro), hydroxy, alkoxy containing 1 to 3 carbon atoms (for example methoxy) or alkyl containing 1 to 3 carbon atoms (for example methyl). When $R_4$ is a heterocyclic ring the ring may contain 5 or 6 atoms. The heterocyclic ring may contain one heteroatom (for example furyl, thienyl, pyrrolyl, pyridyl, tetrahydrofuryl, tetrahydrothienyl, pyrrolinyl, or piperidyl) or more than one heteroatom which may be the same (for example imidazolyl, pyrazolyl, pyrazinyl, pyrimidinyl, pyridazinyl, imidazolidinyl, imidazolinyl, pyrazolidinyl, pyrazolinyl, piperazinyl, triazolyl, tetrazolyl) or different (for example thiazolyl, isoxazolyl, morpholinyl, thiomorpholinyl or the tetrahydro and dihydro derivatives of thiazolyl or isoxazolyl).

When $R_4$ is a carbamoyl group of formula —$CONR_{14}R_{15}$ and $R_{14}$ and/or $R_{15}$ is an alkyl group, the alkyl group may be methyl, ethyl, propyl or isopropyl. When $R_{14}$ and $R_{15}$ together with the nitrogen to which they are attached form a heterocyclic ring, the ring may contain 4, 5 or 6 carbon atoms, one or more of which may be replaced by a further heteroatom in addition to the nitrogen atom to which $R_{14}$ and $R_{15}$ are attached.

When $R_4$ is an alkoxycarbonyl group of formula —$COOR_{16}$, the alkyl group $R_{16}$ may be methyl, ethyl, propyl or isopropyl. When $R_4$ is an amido group of formula $N(R_{17})COR_{18}$, the alkyl groups $R_{17}$ and $R_{18}$ may be a methyl, ethyl or propyl group or, when $R_{17}$ and $R_{18}$ together with the nitrogen atom and carbonyl group to which they are attached form a ring that ring may contain 5 or 6 atoms (for example oxopyrrolidinyl). When $R_4$ is an acyloxy group of formula —$OCOR_{19}$, the alkyl group $R_{19}$ may be a methyl, ethyl or propyl group.

When $R_4$ is a group of formula —$OR_{20}$, $R_{20}$ may be an alkyl group containing 1 to 4 carbon atoms (for example a methyl, ethyl, propyl, isopropyl, butyl or isobutyl group). When $R_4$ is a group of formula —$SR_{20}$, $SOR_{20}$, or $SO_2R_{20}$, $R_{20}$ is an alkyl group containing 1 to 3 carbon atoms (for example a methyl group). When $R_{20}$ is a substituted phenyl group the substituent may be halo (for example fluoro or chloro), hydroxy, alkoxy containing 1 to 3 carbon atoms (for example methoxy) or alkyl containing 1 to 3 carbon atoms (for example methyl).

When $R_5$, $R_6$ or $R_7$ are halo the halo group may be fluoro, chloro, bromo or iodo. When $R_5$, $R_6$ or $R_7$ are alkyl, alkoxy or alkylthio groups the group may contain 1 to 3 carbon atoms (for example methyl, methoxy or methylthio). When $R_5$ and $R_6$ together with the carbon atoms to which they are attached form a second benzene ring, that second benzene ring may optionally be substituted by halo (for example fluoro, chloro or bromo) or by alkyl or alkoxy groups containing 1 to 3 carbon atoms (for example methyl or methoxy) or the substituents on the second benzene ring together with the carbon atoms to which they are attached form a further benzene ring.

When $R_8$ and/or $R_9$ is an alkyl group the group contains 1 to 3 carbon atoms (for example methyl).

When $R_{10}$ and/or $R_{11}$ is halo the halo atom may be fluoro, chloro or bromo. When $R_{10}$ and/or $R_{11}$ is an alkyl or alkoxy group the group contains 1 to 3 carbon atoms (for example methyl or methoxy).

Compounds of formula I may exist as salts with pharmaceutically acceptable acids. Examples of such salts include hydrochlorides, maleates, acetates, citrates, fumarates, tartrates, succinates and salts with dicarboxylic amino acids such as aspartic and glutamic acids. Such salts may exist in the form of solvates (for example hydrates).

Compounds of formula I may contain one or more chiral centres. Compounds having one chiral centre exist in two enantiomeric forms and the present invention includes both enantiomeric forms and mixtures thereof. Compounds having two or more chiral centres exist in diastereoisomeric forms and the present invention includes each of these diastereoisomeric forms and mixtures thereof.

The present invention also includes pharmaceutical compositions containing a therapeutically effective amount of a compound of formula I together with a pharmaceutically acceptable diluent or carrier.

In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1-90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compositions are the excipients known in the pharmacists' art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The active ingredient inside the capsule may be formulated in sustained release form. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example suppositories with cocoa butter or polyethylene glycol bases.

Compositions of the invention suitable for parenteral administration are the known pharmaceutical forms for such administration, for example sterile suspensions in aqueous and oily media or sterile solutions in a suitable solvent.

Compositions for topical administration may comprise a matrix in which the pharmacologically active compounds of the present invention are dispersed so that the compounds are held in contact with the skin in order to administer the compounds transdermally. Alternatively the active compounds may be dispersed in a pharmaceutically acceptable cream or ointment base.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The pharmaceutical compositions containing a therapeutically effective amount of a compound of formula I may be used to treat depression in human beings. In such treatment the amount of the compound of formula I administered per day is in the range 1 to 1000 mg preferably 5 to 500 mg.

Compounds of formula I may be prepared by the reductive amination of ketones or aldehydes of formula IV or V

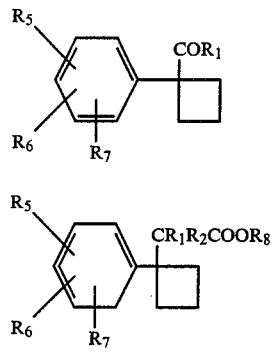

by reaction of the ketone or aldehyde with an amine of formula VI

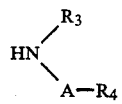

Examples of suitable reductive amination reactions are given below:

(a) by the reaction of the ketone or aldehyde with the amine of formula VI and reducing the resulting imine or enamine for example with sodium borohydride or sodium cyanoborohydride, (b) by the reaction of the ketone or aldehyde with the amine of formula VI in the presence of a reducing agent such as sodium cyanoborohydride or, when $R_3$ is other than H, in the presence of formic acid, (c) when $R_1$ and $R_4$ do not contain reducible double bonds, by the catalytic hydrogenation at elevated temperature and pressure of a mixture of the ketone or aldehyde and the amine of formula VI.

Compounds of formula I in which $R_3$ is H or methyl may be prepared by (a) the reductive amidation of ketones or aldehydes of formula IV or V by the reaction of the ketone or aldehyde with a formamide of formula VII

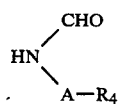

in the presence of formic acid to give compounds of formula VIII

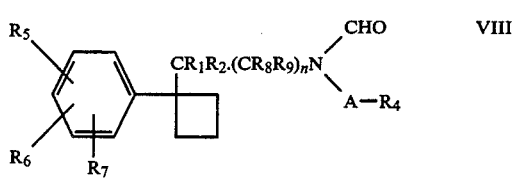

followed by (b) the hydrolysis, for example acid hydrolysis, of the compounds of formula VIII to give compounds of formula I in which $R_3$ is H or the reduction of the compounds of formula VIII for example by lithium aluminium hydride or sodium bis(2-methoxyethoxy)aluminium hydride to give compounds of formula I in which $R_3$ is methyl.

Compounds of formula I may be prepared from amines of formula IX

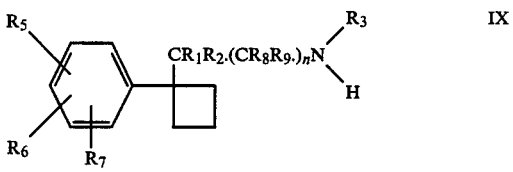

(a) by acylating the amines of formula IX, for example, by reaction with an acyl chloride of formula $R_{21}COCl$ or an anhydride of formula $(R_{21}CO)_2O$ in which $R_{21}$ is a group of formula X $$-(CH_2)_z-W-(CH_2)_y-R_4 \qquad X$$

in which, when W is an oxygen atom or a group of formula $S(O)_m$, z is an integer from 1 to 4 and, when W is a group of formula $-CR_{12}R_{13}-$, a cycloalkylene group, z is 0 or an integer of 1 to 4 and reducing the resulting amides, for example with lithium aluminium hydride, to give compounds of formula I in which A is a group of formula III in which x is $z+1$.

(b) by reacting the amines of formula IX with aldehydes of formula $R_{21}CHO$ and reducing the resulting imines or enamines for example with sodium cyanoborohydride or, when $R_1$, $R_2$, $R_4$, $R_{12}$ and $R_{13}$ do not contain reducible bonds, by catalytic hydrogenation to give compounds of formula I in which A is a group of formula III in which x is $z+1$.

(c) by reacting the amines of formula IX in which $R_3$ is other than H with aldehydes of formula $R_{21}CHO$ in the presence of formic acid to give compounds of formula I in which A is a group of formula III in which x is $z+1$.

(d) by reacting the amines of formula IX with ketones of formula $R_{12}CO(CH_2)_yR_4$ and reducing the resulting imines or enamines for example with sodium cyanoborohydride or, when $R_1$, $R_2$, $R_4$ and $R_{12}$ do not contain reducible double bonds, by catalytic hydrogenation to give compounds of formula I in which A is a group of formula XI —CHR$_{12}$—(CH$_2$)$_y$—     XI (e) by reacting amines of formula IX in which R$_3$ is other than H with ketones of formula R$_{12}$CO(CH$_2$)$_y$R$_4$ in the presence of formic acid to give compounds of formula I in which A is a group of formula XI (f) by acylation of the amines of formula IX with, for example, substituted acyl chlorides of formula R$_{22}$-COCl in which R$_{22}$ is a group of formula XII —(CH$_2$)$_x$—W—(CH$_2$)$_y$—E     XII wherein E is a replaceable group or is convertible thereto and then either (a) reducing the amides so formed and then replacing the group E with the group R$_4$ or (b) replacing the group E with the group R$_4$ and reducing the resulting amides to give compounds of formula I in which A is a group of formula III in which x is z+1. The group E may be for example a halo group which is replaced by the group R$_4$ by reaction with a compound of formula R$_4$H, or a salt derived therefrom. The group E may be a hydroxy group which is converted to a p-toluenesulphonyloxy group which is then replaced by the group R$_4$ by reaction with a compound of formula R$_4$H or a salt derived therefrom.

(g) by reacting the amines of formula IX with a compound of formula XIII

H$_2$C═CH—G     XIII in which G is as defined above in respect of R$_4$ or in respect of E. When G has the meaning defined above in respect of E, the resulting compound is converted into a compound of formula I by methods given above. The following are given as examples of processes of this type.

(i) by reacting the amines of formula IX with vinylpyridine to give compounds of formula I in which A is an ethylene group and R$_4$ is a pyridyl group, (ii) by reacting the amines of formula IX with acrylonitrile to give compounds of formula I in which A is an ethylene group and R$_4$ is a cyano group, (iii) by reacting the amines of formula IX with an alkyl ester of acrylic acid to give compounds of formula I in which A is an ethylene group and R$_4$ is an alkoxycarbonyl group of formula —COOR$_{16}$.

(h) by the reaction of the amines of formula IX with a compound of formula XAR$_4$ in which X is a leaving group such as a halo group (for example a bromo group) or a p-toluenesulphonyloxy group in the presence of a base (for example triethylamine).

Compounds of formula I may be prepared by the reaction of formamides of formula XIV

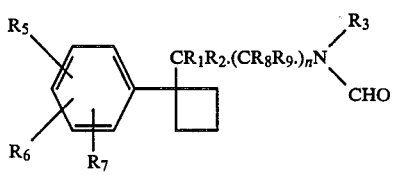

XIV with aldehydes of formula R$_{21}$CHO in the presence of formic acid to give tertiary amines of formula I when R$_3$ is other than H or when R$_3$ is H to give formamides of formula VIII in which A is a group of formula III in which x is z+1 followed by (a) hydrolysis of the formamides of formula VIII, for example acid hydrolysis, to give secondary amines of formula I in which R$_3$ is H or (b) reduction of the formamides of formula VIII, for example by lithium aluminium hydride or sodium bis(2-methoxyethoxy)aluminium hydride to give tertiary amines of formula I in which R$_3$ is methyl.

Compounds of formula I may be prepared by the reaction of formamides of formula XIV with ketones of formula R$_{12}$CO(CH$_2$)$_y$R$_4$ in the presence of formic acid to give tertiary amines of formula I when R$_3$ is other than H, or when R$_3$ is H to give formamides of formula VIII in which A is a group of formula XI followed by (a) hydrolysis of the formamides of formula VIII, for example acid hydrolysis, to give secondary amines of formula I in which R$_3$ is H (b) reduction of the formamides of formula VIII for example by lithium aluminium hydride or sodium bis(2-methoxyethoxy)aluminium hydride to give tertiary amines of formula I in which R$_3$ is methyl.

Compounds of formula I in which n=0 and R$_1$ and R$_2$ are H, and compounds of formula I in which n=1 and R$_8$ and R$_9$ are H may be prepared by the reaction of amines of formula VI with acid derivatives such as esters or acid halides, for example with acid chlorides of formula XV and XVI respectively

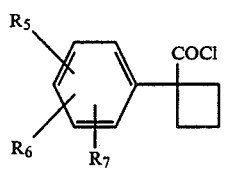

XV

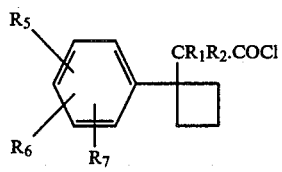

XVI followed by reduction of the resulting amides for example with lithium aluminium hydride or borane methyl sulphide complex.

When the group R$_4$ is a heterocyclic ring containing one nitrogen atom in which the nitrogen atom is bonded directly to the group A, compounds of formula I may be prepared by reacting compounds of formula XVII

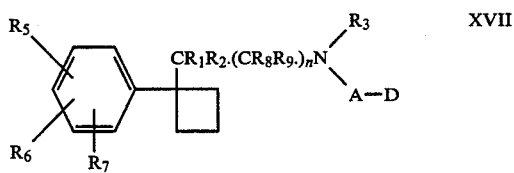

XVII in which D is a group of formula NH$_2$, (a) with a non-geminally disubstituted alkane having at least 2 carbon atoms between the carbon atoms carrying the substituents, which may be halo (for example bromo) or p-toluenesulphonyloxy, to give compounds of formula I in which R$_4$ is a heterocyclic ring containing no heteroatoms other than the nitrogen atom, (b) with a dialkyl ether or thioether in which each alkyl group is substituted by a substituent which may be halo (for example bromo) or p-toluenesulphonyloxy to give compounds of formula I in which R$_4$ is a heterocyclic ring containing an oxygen or sulphur atom in addition to the nitrogen atom or (c) with a dialkylamine in which each alkyl group is substituted by a substituent which may be halo (for example bromo) or p-toluenesulphonyloxy to give compounds of formula I in which $R_4$ is a heterocyclic ring containing a second nitrogen atom.

Compounds of formula I in which $R_4$ is a carbamoyl group of formula —$CONH_2$ may be prepared from compounds of formula I in which $R_4$ is cyano for example by hydration with aqueous acids or by reaction with hydrogen peroxide in the presence of a base. Compounds of formula I in which $R_4$ is an amide group of formula $CONR_{14}R_{15}$ in which one or both of $R_{14}$ and $R_{15}$ are other than H may be prepared by the reaction of amines of formula $HNR_{14}R_{15}$ with carboxylic acid derivatives for example acid chlorides of formula XVII in which D is a group of formula COCl or compounds of formula I in which $R_4$ is an ester group of formula —$COOR_{16}$.

Compounds of formula I in which $R_4$ is an alkoxycarbonyl group of formula —$COOR_{16}$ may be prepared by the esterification of carboxylic acids of formula XVII in which D is a group of formula —COOH.

Compounds of formula I in which $R_4$ is an amido group of formula $N(R_{17})COR_{18}$ may be prepared from compounds of formula XVII in which D is a group of formula —$NH_2$ by either (a) alkylation to introduce the group $R_{17}$ followed by acylation to introduce the group —$COR_{18}$ or (b) by acylation to introduce the group —$COR_{18}$ followed by alkylation to introduce the group $R_{17}$.

Compounds of formula I in which $R_4$ is an acyloxy group of formula $OCOR_{19}$ may be prepared by the acylation of compounds of formula I in which $R_4$ is hydroxy in the form of a salt.

Compounds of formula I in which $R_4$ is a group of formula $SOR_{20}$ may be prepared by the oxidation of compounds of formula I in which R is $SR_{20}$. Compounds of formula I in which $R_4$ is a group of formula $SO_2R_{20}$ may be prepared by the oxidation of compounds of formula I in which $R_4$ is a group of formula $SR_{20}$ or $SOR_{20}$. Methods for these oxidations are well known in the art. Compounds of formula I in which $R_4$ is a group of formula $SO_2R_{20}$ may also be prepared by (a) the oxidation for example using hydrogen peroxide of the product of the reaction between the amines of formula IX and an (alkylthio)-carboxylic acid followed by (b) reduction of the resulting amide for example by borane methyl sulphide complex.

Compounds of formula I in which W is a group of formula $S(O)_m$ and m is 1 may be prepared by the oxidation of compounds of formula I in which m is 0. Compounds of formula I in which m is 2 may be prepared by the oxidation of compounds of formula I in which m is 0 or 1. Methods for these oxidations are well known in the art.

Compounds of formula I may be prepared by the reaction of compounds of formula $R_4H$ or a salt derived therefrom with compounds of formula XVII in which D is a leaving group such as bromo or p-toluenesulphonyloxy. Suitable p-toluene-sulphonyloxy compounds may be prepared from compounds of formula I in which $R_4$ is hydroxy.

Processes suitable for the preparation of the amines of formula IX in which $R_1$ is a group other than a heterocyclic group, the ketones and aldehydes of formula IV in which $R_1$ is a group other than a heterocyclic group and the ketones and aldehydes of formula V and the formamides of formula XIV in which $R_1$ is a group other than a heterocyclic group of formula XII are described in British Patent Application No. 2098602A published after the priority date of the present application. Amines of formula IX, ketones and aldehydes of formula IV and formamides of formula XIV in which $R_1$ is a heterocyclic group may be prepared by methods analogous to those described in the above identified application.

Amines of formula IX in which $R_3$ is H may be prepared by the reduction of compounds of formula XVIII

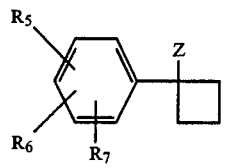

XVIII in which (a) Z is a group of formula —$CR_1$=NH to give compounds of formula IX in which n=0 and $R_2$ is H;

(b) Z is a group of formula —$CONH_2$ to give compounds of formula IX in which n=0 and $R_1$ and $R_2$ are H;

(c) Z is a group of formula —$CR_1R_2.CR_8$=NH to give compounds of formula IX in which n=1 and $R_9$ is H. Suitable reducing agents for the above reactions include sodium borohydride, sodium cyanoborohydride, lithium aluminium hydride or borane-methylsulphide complex.

Amines of formula IX in which $R_3$ is other than H may be prepared by the reduction of compounds of formula XVIII in which Z is a group of formula —$CONHR_3$ to give compounds of formula IX in which n=0 and $R_1$ and $R_2$ are H. Suitable reducing agents for the above reactions include sodium borohydride, sodium cyanoborohydride, lithium aluminum hydride or borane-methylsulphide complex.

Processes suitable for the preparation of acid chlorides of formula XV in which $R_1$ is a group other than the heterocyclic group and the acid chlorides of formula XVI are described in British Patent Application No. 2098602A described above. Acid chlorides of formula XV in which $R_1$ is a heterocyclic group may be prepared by methods analogous to those described in the above identified application.

Compounds of formula XVII may be prepared by similar methods to those described hereinbefore for preparing compounds of formula I but with the $R_4$ group being replaced by D. Compounds of formula XVII in which A is an ethylene group and D is a group of formula $NH_2$ may be prepared by the reaction of compounds of formula IX with nitro-ethylene followed by reduction for example with sodium bis(methoxyethoxy)aluminium hydride. Compounds of formula XVII in which A is a propylene group and D is a $NH_2$ group may be prepared by the reaction of compounds of formula IX with acrylonitrile followed by reduction, for example, with lithium aluminium hydride. Compounds of formula XVII in which A is a propylene group may be prepared by reaction of compounds of formula IX with an ester of acrylic acid followed by (a) reduction of the resulting ester to the corresponding hydroxy compound, (b) replacement of the hydroxy group by a leaving group such as p-toluenesulphonyloxy and (c) replacement of the leaving group by the group D. Compounds of formula XVII in which D is an ester or a group of formula COCl may be prepared by compounds of formula XVII in which D is a group of formula —COOH by methods well known in the art. Compounds of formula XVII in which D is a group of formula —COOH may be prepared by hydrolysis, for example acid hydrolysis, of compounds of formula I in which $R_4$ is a cyano group.

Compounds of formula XVIII in which Z is a group of formula $CR_1$=NH or $CR_1R_2.R_8$=NH may be prepared by the hydrolysis of compounds of formula XVIII in which Z is $CR_1$=NY and $CR_1R_2.CR_8$=NY respectively. In these latter compounds of formula XVIII, Y represents a metal-containing moiety derived from an organometallic reagent such as MgCl or MgBr derived from a Grignard reagent or Li derived from an organolithium compound. Processes suitable for the preparation of these latter compounds in which $R_1$ is other than a heterocyclic group are described in British Patent Application No. 2098602A described above. Compounds of formula XVIII in which Z is a group of formula $CR_1$=NY and $R_1$ is a heterocyclic group may be prepared by methods analogous to those described in the above identified application.

Compounds of formula XVIII in which Z is a group of formula —$CONH_2$ or —$CONHR_3$ may be prepared by the reaction of acid derivatives (for example acid chlorides of formula XV) with ammonia or an amine of formula $R_3NH_2$ respectively. Compounds of formula XVIII in which Z is a group of formula $CONH_2$ may be prepared from cyano compounds of formula XIX

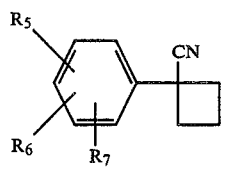

XIX for example by hydration with aqueous acids or by reaction with hydrogen peroxide in the presence of a base.

Processes suitable for the preparation of cyano compounds of formula XIX are described in British Patent Application No. 2098602A described above.

The therapeutic activity of the compounds of formula I has been indicated by assessing the ability of the compounds to reverse the hypothermic effects of reserpine in the following manner. Male mice of the Charles River CD1 strain weighing between 18 and 30 grammes were separated into groups of five and were supplied with food and water ad libitum. After five hours the body temperature of each mouse was taken orally and the mice were injected intraperitoneally with reserpine (5 mg/kg) in solution in deionised water containing ascorbic acid (50 mg/ml). The amount of liquid injected was 10 ml/kg of body weight. Nine hours after the start of the test food was withdrawn but water was still available ad libitum. Twenty-four hours after the start of the test the temperatures of the mice were taken and the mice were given the test compound suspended in a 0.25% solution of hydroxy ethyl cellulose (sold under the trade name Cellosize QP 15000 by Union Carbide) in deionised water at a dose volume of 10 ml/kg of body weight. Three hours later the temperatures of all the mice were again taken. The percentage reversal of the reserpine-induced loss of body temperature is then calculated by the formula:

$$\frac{(T_{27} - T_{24})}{(T_5 - T_{24})} \times 100$$

in which $T_t$ is the temperature in degrees Celsius after t hours. The mean value for each group of five mice was taken at several dose rates to enable a value of the mean dose which causes a 50% reversal (ED50) to be obtained. All the compounds which are the final products of the Examples hereinafter gave values of ED50 of 30 mg/kg or less. It is widely understood by those skilled in the art that this test is indicative of compounds having antidepressant activity in humans.

The invention will now be illustrated by the following Examples which are given by way of example only. All compounds were characterised by conventional analytical techniques and gave satisfactory elemental analyses. All melting and boiling points are expressed in degrees Celsius.

EXAMPLE 1

1-Acetyl-1-(3,4-dichlorophenyl)cyclobutane (4.86 g) and benzylamine (2.2 ml) were stirred at a temperature of 140° to 150° C. under nitrogen for 1 hour 30 minutes. Methanol (50 ml) was added to the cooled reaction mixture and sodium borohydride (0.8 g) was added over a period of ten minutes. The mixture was stirred at ambient temperature for two hours and then the volume of the reaction mixture was reduced by a half and the mixture poured into water (300 ml). The aqueous mixture was extracted with ether and the ether extract dried and the ether removed by evaporation. The residue was distilled (b.p. 182°–186° at 0.5 mm Hg) and the distillate treated with hydrogen chloride in ether to give N-benzyl-1-[1-(3,4-dichlorophenyl)cyclobutyl]ethylamine hydrochloride (m.p. 227°–228° C.).

EXAMPLES 2 TO 37

In a similar manner to that described in Example 1 the compounds of formula XX listed in Table 1 and the compounds of formula XXI listed in Table 2 were prepared Columns I and II of these Tables show the time in hours and temperature in degrees Celsius at which the reaction between the ketone and the amine took place.

TABLE 1

Structure XX: 3,4-dichlorophenyl-cyclobutyl-C(Me)H-NH(CH$_2$)$_x$W(CH$_2$)$_y$R$_4$

| Example Number | x | y | W | R$_4$ | I | II | mp (°C.) | Notes |
|---|---|---|---|---|---|---|---|---|
| 2 | 0 | 0 | CH$_2$ | 2-thienyl | 2 | 140 | 224–226° | (3) |
| 3 | 0 | 0 | CH$_2$ | 2-pyridyl | 2 | 140 | 236–238°(dec) | (4) |
| 4 | 0 | 0 | CH$_2$ | 3-pyridyl | 2 | 140 | 253–255° | (4) |
| 5 | 0 | 0 | CH$_2$ | 4-pyridyl | 2 | 130 | 234–238°(dec) | (4) |
| 6 | 0 | 0 | CH$_2$ | 2-furyl | 2 | 140 | 204–207° | (3) |
| 7 | 0 | 0 | CH$_2$ | 2-tetrahydrofuryl | 2 | 130–150 | | (1) |
| 8 | 0 | 1 | CH$_2$ | morpholino | 2 | 130 | 154°(dec) | (4) |
| 9 | 0 | 1 | CH$_2$ | 2-pyridyl | 2 | 130 | 165°(dec) | (4) |
| 10 | 0 | 1 | CH$_2$ | 4-pyridyl | 2 | 140 | 198–208°/0.5 mm Hg | (2) |
| 11 | 0 | 1 | CH$_2$ | piperidino | 2 | 140 | 164–168°/0.2 mm Hg | (2) |
| 12 | 0 | 1 | CH$_2$ | phenyl | 3 | 140–150 | 95°(dec) | (3) |
| 13 | 0 | 1 | CH$_2$ | 4-imidazolyl | 3 | 140 | 164–170°(dec) | (4) |
| 14 | 0 | 1 | CH$_2$ | p-chlorophenylthio | 4½ | 140 | 209–211°/0.1 mm Hg | (2) |
| 15 | 0 | 1 | CH$_2$ | cyclohept-1-enyl | 16 | 140 | 179–180°/0.1 mm Hg | (2) |
| 16 | 0 | 1 | CH$_2$ | OH | 2 | 140 | 168–173° | (3) |
| 17 | 0 | 1 | CH$_2$ | OMe | 20 | 95 | 145–146°/0.5 mm Hg | (2) |
| 18 | 0 | 1 | CHMe | phenoxy | 4 | 140 | 192–194°/0.2 mm Hg | (2) |
| 19 | 0 | 1 | CHEt | OH | 18 | 140 | 163°/0.2 mm Hg | (2)(5) |
| 20 | 0 | 1 | CH$_2$ | CN | 5 | 120–130 | 200° | (3) |
| 21 | 0 | 2 | CH$_2$ | 1-imidazolyl | 2 | 140 | 232–236°/0.5 mm Hg | (2) |
| 22 | 0 | 2 | CH$_2$ | morpholino | 2 | 140 | 170–175° | (4)(8) |
| 23 | 0 | 2 | CH$_2$ | 1-pyrrolidin-2-onyl | 2 | 140 | 218–219° | (3) |
| 24 | 0 | 2 | CH$_2$ | OH | 2 | 140 | 162–165° | (3)(8) |
| 25 | 0 | 2 | CH$_2$ | OMe | 4 | 100–120 | 157°/0.4 mm Hg | (2) |
| 26 | 0 | 2 | CH$_2$ | OEt | 4 | 125 | 158°/0.4 mm Hg | (2) |
| 27 | 0 | 2 | CH$_2$ | O$^i$Pr | 18 | 135 | 145–146°/0.05 mm Hg | (2) |
| 28 | 0 | 2 | CH$_2$ | OBu | 3 | 140 | 180°/0.1 mm Hg | (2) |
| 29 | 0 | 3 | CH$_2$ | OH | 3 | 140 | 182°/0.4 mm Hg | (2) |
| 30 | 1 | 0 | CH(OMe) | OMe | 3 | 130–140 | 146°/0.4 mm Hg | (2) |
| 31 | 1 | 0 | CHMe | OH | 2 | 140 | 184–186°(dec) | (3)(8) |
| 32 | 1 | 1 | CH(OH) | 1,2,4-triazol-1-yl | 3 | 140 | 257–261° | (4) |
| 33 | 2 | 2 | O | OH | 2 | 140 | 180–182°/0.3 mm Hg | (2) |
| 34 | 2 | 2 | S | OH | 3 | 140 | 202–205°/0.2 mm Hg | (2) |

TABLE 2

Structure XXI: R$_5$, R$_6$, R$_7$ substituted phenyl-cyclobutyl-C(Me)H-NHCH$_2$)$_p$R$_4$

| Example Number | R$_5$ | R$_6$ | R$_7$ | p | R$_4$ | I | II | mp(°C.) | Notes |
|---|---|---|---|---|---|---|---|---|---|
| 35 | H | H | H | 1 | 4-pyridyl | 2 | 140 | 224° | (8)(9) |
| 36 | H | H | H | 2 | morpholino | 2 | 140 | 147–153°/0.4–0.5 mm Hg | (2) |
| 37 | 4-Cl | H | H | 2 | morpholino | 3 | 130 | 148–150°(dec) | (4)(8) |

Notes on Tables
(1) product purified by high pressure liquid chromatography. Physical constants not determined.
(2) boiling point of free base.
(3) monohydrochloride salt.
(4) dihydrochloride salt.
(5) L-form.
(6) dimaleate salt.
(7) monomaleate salt.
(8) monohydrate.
(9) contains 1.45 moles HCl per mole.
(10) hemihydrate.
(11) physical constants not determined but the structure of the compound was confirmed by conventional analytical techniques
(12) solvent for the reduction stage was ethanol
(13) solvent for the reduction stage was methanol
(14) solvent for the reduction stage was a mixture of ethanol and methanol.

EXAMPLE 38

1-Acetyl-(3,4-dichlorophenyl)cyclobutane (5.0 g) was added to 2-n-propoxyethylamine (1.9 g) and the mixture was stirred and heated to 140°–145° C. with a slow stream of nitrogen blowing over the reaction to remove the water produced. Heating was continued for 20 hours. The mixture was cooled and a suspension of sodium borohydride (707 mg) in propan-2-ol (60 ml) was added and the mixture heated under reflux for 16 hours. The solvent was removed and the residue was treated with water (150 ml) and the product extracted into ether. The extract was washed with water (10×75 ml) dried, filtered and a solution of maleic acid (2.13 g) in ether (100 ml) was added. The mixture was cooled, the resultant solid recrystallised from industrial methylated spirit to give N-(2-propoxyethyl)-1-[1-(3,4-dichlorophenyl)cyclobutyl]ethylamine maleate (m.p. 112°–114° C.).

EXAMPLE 39

In a similar manner to that described in Example 38 the compounds of formula XX listed in Table 3 and the compounds of formula XXI listed in Table 4 were prepared. The Notes have the same meaning as those given in Tables 1 and 2.

TABLE 3

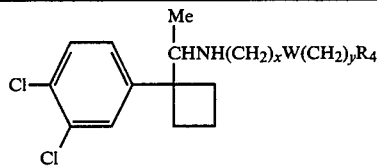

XX

| Example Number | x | y | W | $R_4$ | I | II | mp (°C.) | Notes |
|---|---|---|---|---|---|---|---|---|
| 39 | 0 | 1 | $CH_2$ | thiomorpholino | 24 | 140 | 120–122° (dec) | (4) (12) |
| 40 | 0 | 1 | CHPr | OH | 26 | 160 | 143–145° | (7) (13) |
| 41 | 0 | 2 | $CMe_2$ | OH | 20 | 140 | 128–130° | (7) |
| 42 | 2 | 1 | S | phenyl | 4 | 140 | 163–166° | (3) (12) |
| 43 | 2 | 1 | S | 2-chloro-6-fluorophenyl | 20 | 140 | 152–154° | (7) |
| 44 | 2 | 2 | O | OMe | 8 | 110 | 119–120° | (7) (12) |

TABLE 4

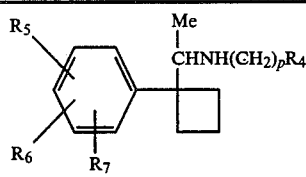

XXI

| Example Number | $R_5$ | $R_6$ | $R_7$ | p | $R_4$ | I | II | mp(°C.) | Notes |
|---|---|---|---|---|---|---|---|---|---|
| 45 | 4-SMe | H | H | 2 | morpholino | 24 | 160 | 156–158° | (6) (13) |
| 46 | 4-Br | H | H | 2 | morpholino | 8 | 140 | 179–180° | (6) (13) |
| 47 | 4-Ph | H | H | 2 | morpholino | 18 | 140 | 145–147° | (6) (13) |
| 48 | 4-Ph | H | H | 2 | OH | 18 | 140 | 103–107° | (7) (13) |
| 49 | 4-I | H | H | 2 | OMe | 20 | 95 | 170–175° | (3) (12) |
| 50 | 4-I | H | H | 2 | morpholino | 20 | 140 | 155–160° | (3) (10) (12) |
| 51 | 3,4-benzo | | H | 2 | morpholino | 6½ | 150 | 162–164° | (6) (13) |
| 52 | 3,4-benzo | | H | 2 | OH | 6½ | 150 | 110–112° | (7) (13) |

EXAMPLE 53

In a similar manner to that described in either Example 1 or Example 38 the compounds of formula XXII listed in Table 5 and the compounds of formula XXIII listed in Table 6 were prepared. The Notes have the same meanings as those given for Tables 1 and 2.

TABLE 5

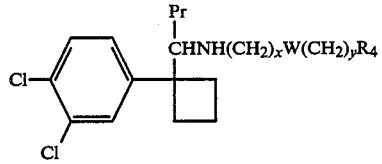

XXII

| Example Number | x | y | W | $R_4$ | I | II | Method | mp (°C.) | Notes |
|---|---|---|---|---|---|---|---|---|---|
| 53 | 0 | 0 | $CH_2$ | 4-pyridyl | 2 | 135 | as Ex 1 | 211–213°(dec) | (4)(8) |
| 54 | 0 | 0 | 1,2-cyclohexylene | OH | 24 | 160 | as Ex 38 | 189–191° | (3)(13) |
| 55 | 0 | 1 | $CH_2$ | morpholino | 2½ | 140 | as Ex 1 | 246–248° | (4)(8) |
| 56 | 0 | 1 | $CH_2$ | OPh | 16 | 140 | as Ex 1 | | (1) |
| 57 | 0 | 1 | $CH(CH_2Ph)$ | OH | 24 | 160 | as Ex 38 | 144–146°(dec) | (3)(14) |
| 58 | 1 | 0 | Cyclohexylidene | OH | 24 | 160 | as Ex 38 | 195–196° | (3)(13) |
| 59 | 0 | 4 | $CH_2$ | OH | 12 | 140 | as Ex 1 | 201–205°/0.05 mm Hg | (2) |
| 60 | 2 | 2 | O | OH | 5 | 160 | as Ex 1 | 198–200°/0.5 mm Hg | (2) |
| 61 | 2 | 2 | S | OH | 3 | 140 | as Ex 1 | 190°/0.05 mm Hg | (2)(13) |
| 62 | 3 | 2 | $CH_2$ | OH | 17 | 160 | as Ex 38 | 120–123° | (7)(13) |

TABLE 5-continued

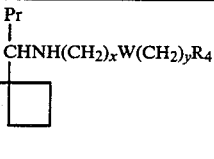

XXII

| Example Number | x | y | W | $R_4$ | I | II | Method | mp (°C.) | Notes |
|---|---|---|---|---|---|---|---|---|---|
| 63 | 4 | 3 | $CH_2$ | OH | 17 | 160 | as Ex 38 | | (11)(13) |

TABLE 6

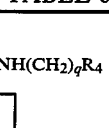

XXIII

| Example Number | Ar | q | $R_4$ | I | II | Method | b.p./m.p. | Notes |
|---|---|---|---|---|---|---|---|---|
| 64 | 2-fluorophenyl | 2 | morpholino | 5 | 140 | as Ex 38 | 150°/0.01 mm Hg | (2) |
| 65 | 3-trifluoromethylphenyl | 2 | morpholino | 4.75 | 140 | as Ex 38 | 140°/0.05 mm Hg | (2) |
| 66 | 6-chloronaphth-2-yl | 2 | morpholino | 18 | 140 | as Ex 38 | 168–169° | (6)(13) |

EXAMPLE 67

In a similar manner to that described in Example 38, N-(2-methoxyethyl)-1-[1-(3,4-dichlorophenyl)cyclobutyl]-2-methylpropylamine hydrochloride (m.p. 158°–160° C.) was prepared.

EXAMPLE 68

A mixture of 1-acetyl-1-(3,4-dichlorophenyl)cyclobutane (2.43 g), glycinamide hydrochloride (2.21 g) powdered potassium hydroxide (1.2 g) and sodium cyanoborohydride (1.5 g) in methanol (20 ml) was stirred at 0°–5° C. for 2 hours then for a total of 10 days at ambient temperature. The mixture was cooled and 5N hydrochloric acid added. The mixture was then basified, extracted into ether, washed with water, dried and evaporated to give an oil. This oil was dissolved in ether and a solution of maleic acid (1.0 g) in dry ether (100 ml) was added to give an oil which was dissolved in acetone. Ether was then added to give a white solid which was dissolved in water, basified and extracted into ether. Passing hydrogen chloride gas through the dried ethereal extract gave 2-{1-[1-(3,4-dichlorophenyl)cyclobutyl]ethylamino}acetamide hydrochloride (m.p. 240°–245° C.).

EXAMPLE 69

A mixture of 2-(4-methoxyphenoxy)ethylamine (7.0 g) 1-butyryl-1-(3,4-dichlorophenyl)cyclobutane (10.8 g) and dibutyltin dichloride (0.61 g) in dry toluene (20 ml) was stirred and refluxed for 2 hours. Toluene was removed by evaporation and the mixture heated at 175°–180° C. for a total of 7 hours. The mixture was cooled, dissolved in absolute ethanol (25 ml) then added to a solution of sodium borohydride (5 g) in ethanol (250 ml) and the mixture heated under reflux for 2 hours. The ethanol was evaporated and the mixture acidified, basified and extracted into ether. Passage of hydrogen chloride gas through the dried extracts gave a sticky solid which was partitioned between ether and 5N sodium hydroxide solution. The ether layer was washed with 5N hydrochloric acid, basified, extracted into ether and dried. A solution of maleic acid (3 g) in dry ether (300 ml) was added to give N-[2-(4-methoxyphenoxy)ethyl]-1-[1-(3,4-dichlorophenyl)cyclobutyl]butylamine maleate (m.p. 164°–166° C.).

EXAMPLE 70

A mixture of the compound of Example 37 in the form of its free base (3.2 g), 98% formic acid (2 ml), 37–40% aqueous formaldehyde (2.8 ml) and water (0.28 ml) was heated at 90° to 95° C. for eighteen hours. After cooling, concentrated hydrochloric acid (1 ml) was added and the reaction mixture evaporated to dryness. The residue was triturated with ether to yield N-methyl-N-(2-morpholinoethyl)-1-[1-(4-chlorophenyl)cyclobutyl]ethylamine dihydrochloride hydrate [m.p. 225°–228° C. (dec)].

EXAMPLE 71

A stirred mixture of p-anisaldehyde (0.62 ml) and 1-[1-(3,4-dichlorophenyl)cyclobutyl]ethylamine (see Example 1 of published British Patent Specification No. 2098602) in the form of its free base (1.22 g) was heated to 130°–135° for 30 minutes. After cooling the residue was dissolved in ethanol (10 ml) and the solution added to a solution of sodium borohydride (1.5 g) in ethanol (200 ml). The mixture was heated under reflux for one hour. Water (10 ml) and then excess 5N HCl were added and the ethanol removed by evaporation. The residue was basified with aqueous sodium hydroxide solution and an ether extraction performed. The extract was dried and evaporated to give an oil. Hydrogen chloride gas was passed through an ethereal solution of the oil to give N-(4-methoxybenzyl)-1-[1-(3,4-dichlorophenyl)cyclobutyl]ethylamine hydrochloride (m.p. 217°–218° C.).

EXAMPLE 72

In a similar manner to that described in Example 71 N-(4-fluorobenzyl)-1-[1-(3,4-dichlorophenyl)cyclobutyl]ethylamine hydrochloride (m.p. 244°–245° C.) was prepared.

EXAMPLE 73

A solution of p-anisaldehyde (6.43 g) and 1-[1-(4-chlorophenyl)cyclobutyl]ethylamine (see Example 1(b) of published British Patent Specification No. 2098602) in the form of its free base (9.09 g) in dry toluene (50 ml) was heated under reflux for 20 hours under nitrogen and water was removed by means of a Dean-Stark apparatus. The reaction mixture was cooled and solid sodium borohydride (4.1 g) was added. Methanol (40 ml) was added dropwise at a temperature of 25°–30° C. The mixture was heated under reflux for one hour and the methanol and toluene removed by evaporation. The residue was cooled to ambient temperature and excess 5N hydrochloric acid added. The mixture was then basified with aqueous sodium hydroxide solution and extracted with ether. The ether extract was washed and shaken with 5N hydrochloric acid to give a white solid which was recrystallised from ethanol to give N-(4-methoxybenzyl)-1-[1-(4-chlorophenyl)cyclobutyl]ethylamine hydrochloride (m.p. 225°–228° C.).

EXAMPLE 74

A solution of 1-(3,4-dichlorophenyl)-1-cyclobutanecarbonitrile (28.5 g) in dry ether (200 ml) was added dropwise in a nitrogen atmosphere to a stirred mixture of lithium aluminium hydride (6.5 g) and dry ether (200 ml). The mixture was stirred at room temperature for two hours then it was cooled to 10° C. Water (12 ml) and then 15% aqueous sodium hydroxide solution (12 ml) and then water (36 ml) were added. The mixture was filtered through diatomaceous earth (trade name CELITE). The filter was washed with ether and the combined ether phases were washed with water and dried. Hydrogen chloride gas was passed into the solution to give [1-(3,4-dichlorophenyl)cyclobutyl]methylamine hydrochloride (m.p. 271°–272° C.).

A solution of chloroacetylchloride (3 g) in dry ether was added dropwise to a stirred solution of [1-(3,4-dichlorophenyl)cyclobutyl]methylamine (6.2 g prepared from the hydrochloride salt described above) and triethylamine (2.9 g) in dry ether (20 ml) at a temperature of 5° to 10° C. The mixture was stirred for four hours, filtered and the filtrate washed with water, dried and evaporated to give N-(2-chloroacetyl)[1-(3,4-dichlorophenyl)cyclobutyl]methylamine (m.p. 104°–105° C.).

A solution of morpholine (1.9 ml) in dry tetrahydrofuran (5 ml) was added dropwise to a solution of the chloroacetyl compound (2.7 g) in dry tetrahydrofuran (10 ml) and the mixture was heated under reflux for two hours. The mixture was filtered and the filtrate evaporated to dryness. The residue was dissolved in ether and the solution washed with water and dried. Passing hydrogen chloride gas through the dried solution gave N-{[1-(3,4-dichlorophenyl)cyclobutyl]methyl}-2-morpholinoacetamide hydrochloride (m.p. 195°–198° C.).

Borane-methyl sulphide complex (2 ml) was added to a refluxing solution of the morpholinoacetamide prepared in a similar manner to that described above in the form of its free base (3.6 g) in dry tetrahydrofuran (20 ml) and the mixture heated under reflux for four hours. The mixture was cooled and water (10 ml) added. Dimethylsulphide and tetrahydrofuran were removed by evaporation and excess 5N hydrochloric acid added. The solution was basified and extracted with ether. Hydrogen chloride gas was passed into the washed and dried ether extract. Evaporation to dryness gave a residue which was triturated with dry ether and recrystallised from an 8:2 mixture of propan-2-ol and ethanol to give N-(2-morpholinoethyl)-[1-(3,4-dichlorophenyl)cyclobutyl]methylamine dihydrochloride monohydrate (m.p. 230°–244° C.).

EXAMPLE 75

A solution of chloroacetylchloride (5.5 g) in dry ether (30 ml) was added dropwise to a solution of α-[1-(4-chlorophenyl)cyclobutyl]benzylamine (see Example 16 of published British Patent Specification No. 2098602) in the form of its free base (11.95 g) and a solution of triethylamine (4.9 g) in dry ether (40 ml) at around 5° C. The mixture was stirred at room temperature for twenty hours and then filtered. The filtrate was washed with water, aqueous sodium bicarbonate solution and water and dried over magnesium sulphate. Morpholine (8.4 g) was added and the mixture heated under reflux for 24 hours. The reaction mixture was extracted with 2N hydrochloric acid and the aqueous fraction washed with ether. Addition of aqueous sodium hydroxide precipitated a solid which was recrystallised from petroleum ether (b.p. 80°–100° C.) to give N-{α-[1-(4-chlorophenyl)cyclobutyl]benzyl}-2-morpholinoacetamide (m.p. 95°–97° C.).

Borane-methyl sulphide complex (11.5 ml) was added dropwise under nitrogen to a solution of the acetamide prepared above (6 g) in dry tetrahydrofuran (50 ml) heated under reflux. Heating under reflux was continued for 16 hours and excess reducing agent and solvent removed by distillation. The residue was cooled and water (60 ml) and excess 5N hydrochloric acid added. Aqueous sodium hydroxide solution was added with ice-cooling and the mixture extracted with ether. The ether extract was washed and dried and hydrogen chloride gas passed into it to give a precipitate which was dissolved in hot ethanol. Addition of petroleum ether (b.p. 60°–80°) precipitated N-(2-morpholinoethyl)-α-[1-(4-chlorophenyl)cyclobutyl]benzylamine dihydrochloride (m.p. 235°–240° C.).

EXAMPLE 76

Thionyl chloride (6 ml) was added to 2-[1-(4-chlorophenyl)cyclobutyl]acetic acid (1.5 g) (see Example 38 of published British Patent Specification No. 2098602) and the mixture heated under reflux for one hour. Excess thionyl chloride was removed in vacuo and the residue added dropwise with cooling to a solution of 2-methoxyethylamine (0.99 g) in ether (10 ml). The mixture was stirred for 30 minutes and water added. The ether phase was washed with water, dried and the solvent removed by evaporation to give N-(2-methoxyethyl)-2-[1-(4-chlorophenyl)cyclobutyl]acetamide.

Borane-methyl sulphide complex (3.4 ml) was added dropwise to a solution of the acetamide (1.6 g) prepared as described above in dry tetrahydrofuran (30 ml). The mixture was heated under reflux for seven hours and then half the solvent removed by evaporation. A mixture of concentrated hydrochloric acid (5 ml) and water (5 ml) was added dropwise with ice-cooling. Water was added and the aqueous layer washed with ether, cooled in ice, basified with 16N sodium hydroxide solution and extracted with ether. The ether extract was washed, dried and the ether removed by evaporation. Hydrogen chloride gas was passed into a solution of a sample of the residue in ether to give N-(2-methoxyethyl)-2-[1-(4-chlorophenyl)cyclobutyl]ethylamine hydrochloride (m.p. 113°–115° C.).

EXAMPLE 77

In a similar manner to that described in Example 76, N-(2-methoxyethyl)-2-[1-(2-naphthyl)cyclobutyl]ethylamine was prepared and isolated as its meleate salt (m.p. 95°–99° C.) by adding a solution of maleic acid (2.5 g) in ether (500 ml) to a solution of the free base (0.5 g) in ether (20 ml).

EXAMPLE 78

Dicyclohexylcarbodiimide (3.62 g) was added to a stirred solution of 1-[1-(3,4-dichlorophenyl)cyclobutyl]ethylamine (see Example 1 of published British Patent Application No. 2098602) in the form of its free base (4.02 g) and (methylthio)acetic acid (1.8 g) in dichloromethane (100 ml). The mixture was stirred at ambient temperature for six hours then filtered through diatomaceous earth (sold under the trade name CELITE) and the solvent removed by evaporation. Petroleum ether (500 ml b.p. 60°–80°) at its boiling point was added and the mixture filtered. The volume of the filtrate was reduced to ca 200 ml and the solution was cooled to 0° C. N-{1-[1-(3,4-dichlorophenyl)cyclobutyl]ethyl}-2-(methylthio)acetamide (m.p. 88° C.) precipitated as white needles.

Borane-methyl sulphide complex (14 ml) was added dropwise to a solution of the acetamide prepared as described above (7.6 g) in dry tetrahydrofuran (10 ml) heated under reflux. Heating was continued for six hours and the mixture was left at room temperature for sixty hours. Crushed ice (200 g) was added cautiously followed by 5N hydrochloric acid added dropwise to pH 2. The mixture was basified with aqueous sodium hydroxide solution and the volume reduced by evaporation. The mixture was extracted with ether and the extracts washed and dried. Hydrogen chloride gas was passed into the extract and the solvent removed by evaporation. The residue was heated with petroleum ether (b.p. 60°–80° C.) to give N-[2-(methylthio)ethyl]-1-[1-(3,4-dichlorophenyl)cyclobutyl]ethylamine hydrochloride (m.p. 148°–150° C.).

EXAMPLE 79

A mixture of the product of Example 78 in the form of its free base (5.7 g), m-chloroperbenzoic acid (3.7 g-85% purity) and dichloromethane (300 ml) was stirred at ambient temperature for 12 hours. The reaction solution was washed with 5N aqueous sodium hydroxide solution and water and then dried. Evaporation of the solvent gave an oil from which N-[2-(methylsulphinyl)ethyl]-1-[1-(3,4-dichlorophenyl)cyclobutyl]ethylamine was separated by high pressure liquid chromatography. The amine was dissolved in dry ether and hydrogen chloride gas passed through the solution to give a gum which was dissolved in ethyl acetate. Heating this solution to 80° C. caused the precipitation of N-[2-(methylsulphinyl)ethyl]-1-[1-(3,4-dichlorophenyl)cyclobutyl]ethylamine hydrochloride (m.p. 170°–171° C.).

EXAMPLE 80

N-{1-[1-(3,4-dichlorophenyl)cyclobutyl]ethyl}-2-(methylthio)acetamide prepared as described in Example 77 (4.1 g) was added to a vigorously stirred solution of sodium tungstate (10 mg) and glacial acetic acid (4 drops) in water (20 ml). 27.5% Aqueous hydrogen peroxide solution (3.2 ml) was added dropwise and the mixture stirred at 80° C. for four hours. The reaction mixture was left at ambient temperature for 16 hours. Aqueous ammonia solution (S.G. 0.880 2 ml) was added and then sodium metabisulphite was added in small portions until gas evolution ceased. The mixture was extracted with dichloromethane and the solvent removed to yield a residue which was shown by gas-liquid chromatography (glc) to contain 45% of the desired product. The residue was treated twice in the above procedure until glc showed 85% of the desired product. The final residue was purified by chromatography to give a white solid (m.p. 167°–169°) which is believed to be N-1-[1-(3,4-dichlorophenyl)cyclobutyl]ethyl-2-(methylsulphonyl)acetamide.

Borane-methyl sulphide complex (1.34 ml) was added dropwise to a mixture of the acetamide prepared as described above (1.47 g) and tetrahydrofuran (6 ml) heated under reflux. Heating was continued for 3 hours and the mixture was then kept at ambient temperature for 16 hours before being cooled in ice. Water (50 ml) was added dropwise and the solution was made acidic by the addition of 5N hydrochloric acid. After basifying the solution with aqueous sodium hydroxide an ether extraction was performed. Hydrogen chloride gas was passed into the dried ether extract. The ether was removed by evaporation and the residue dissolved in ethyl acetate. N-[2-(methylsulphonyl)ethyl]-1-[1-(3,4-dichlorophenyl)cyclobutyl]ethylamine hydrochloride (m.p. 172°–174° C.) crystallised from the solution.

EXAMPLE 81

The product of Example 74 in the form of its free base (0.55 g) 98% formic acid (4 ml) and 37–40% aqueous formaldehyde were heated at 70°–80° C. for four hours. The reaction mixture was cooled and basified with aqueous sodium hydroxide solution. The mixture was then extracted with ether and the ether extract washed and dried. Hydrogen chloride gas was passed through the extract to give N-methyl-N-(2-morpholinoethyl)-[1-(3,4-dichlorophenyl)cyclobutyl]methylamine dihydrochloride (m.p. 233°–235° C.).

EXAMPLE 82

In a similar manner to that described in Example 81 the product of Example 77 in the form of its free base was converted into N-(2-methoxyethyl)-N-methyl-2-[1-(2-naphthyl)cyclobutyl]ethylamine hydrochloride (m.p. 139°–141° C.).

EXAMPLE 83

In a similar manner to that described in Example 81 the product of Example 20 in the form of its free base was converted into N-methyl-3-{1-[1-(3,4-dichlorophenyl)cyclobutyl]ethylamino}propiononitrile hydrochloride (m.p. 219°–220° C.).

EXAMPLE 84

4-Pyridinecarboxaldehyde (2.35 g) was added to a mixture of 1-[1-(4-chlorophenyl)cyclobutyl]-3-methylbutylamine (5 g) and dibutyltin dichloride (0.63 g) in toluene (15 ml) and the resulting mixture was heated under reflux for 17 hours. The mixture was cooled and dissolved in ethanol (50 ml). A suspension of sodium borohydride (5 g) in ethanol (250 ml) was added slowly. The mixture was stirred and heated under reflux for 2 hours and was then allowed to cool overnight. Water (75 ml) was added slowly followed by 5N hydrochloric acid (25 ml) and the alcohol was then removed by evaporation. The aqueous residue was cooled and washed with ether. The aqueous solution was basified with 16N aqueous sodium hydroxide and the product extracted with ether. The extracts were washed with water, dried and evaporated to give an oil.

The residue was purified by a process in which the residue was dissolved in toluene (50 ml) and extracted with 5N hydrochloric acid (4×). The extracts were washed with toluene and basified and the product was extracted with ether.

The dried ethereal solution was treated with hydrogen chloride gas to give a solid with was collected, suspended in boiling ethyl acetate and industrial methylated spirit was added to give a clear solution. N-(4-pyridylmethyl)-1-[1-(4-chlorophenyl)cyclobutyl]-3-methylbutylamine dihydrochloride [(m.p. 201°-205° C. (dec)] crystallised on cooling.

EXAMPLE 85

1-[1-(4-Methoxyphenyl)cyclobutyl]ethylamine (2.8 g) was heated to 120° C. and 4-pyridinecarboxaldehyde (2.1 g) was added and the mixture was heated at 120°-200° C. for 2 hours. The mixture was allowed to cool and diluted with methanol. Sodium borohydride (1.75 g) was added and the resulting mixture heated under reflux for 2½ hours. After standing at room temperature for 16 hours the mixture was poured into water, treated with 5N hydrochloric acid and then basified with 5N aqueous sodium hydroxide solution. The product was extracted into ether and the ether extracts were washed with water, dried and evaporated to dryness to give a red oil. The oil was purified by distillation and the distillate dissolved in ether and treated with a solution of excess maleic acid in ether to give a white solid and a sticky yellow gum. Recrystallisation of the white solid from propan-2-ol and ether gave N-(4-pyridylmethyl)-1-[1-(4-methoxyphenyl)cyclobutyl]-ethylamine (1.25) maleate as a pale yellow solid (m.p. 110°-113° C.).

EXAMPLE 86

A mixture of 1-[1-(3-chloro-4-methylphenyl)cyclobutyl]butylamine (2.5 g) [see Example 10(k) of British Patent Specification No. 2098602A] and 4-pyridinecarboxaldehyde (1.5 ml) was stirred and heated at 130° C. for 18 hours. The mixture was dissolved in ethanol (50 ml) and the solution added to a solution of sodium borohydride (2.5 g) in ethanol (120 ml) and heated under reflux for 2 hours. Excess ethanol was removed by evaporation and the mixture acidified, basified and extracted into ether. Hydrogen chloride gas was passed through the dried extract to give an oil which was triturated with acetone to give N-(4-pyridylmethyl)-1-[1-(3-chloro-4-methylphenyl)cyclobutyl]-butylamine dihydrochloride (m.p. 203°-206° C.).

EXAMPLE 87

In a similar manner to that described in Example 86 above except that the reduction took place in methanol at ambient temperature, N-(4-pyridylmethyl)-1-[1-(4-chlorophenyl)-cyclobutyl]butylamine dihydrochloride (m.p. 228°-230° C.) as prepared.

EXAMPLE 88

Sodium borohydride (2.5 g) was added portionwise to a stirred solution of methoxyacetic acid (26.4 g) in toluene (300 ml) under an atmosphere of nitrogen and stirring was continued for 16 hours. A solution of 1-[1-(4-chlorophenyl)cyclobutyl]-3-methylbutylamine (5 g) in toluene (50 ml) was then added and the mixture was heated under reflux with stirring for 24 hours. After cooling the reaction mixture, water (200 ml) was added and the mixture was basified with 16N aqueous sodium hydroxide solution. The product was extracted into ether and the extracts were washed with water, dried and evaporated to give a brown oil which was dissolved in ether (30 ml). A solution of maleic acid (4.8 g) in ether (250 ml) was added. The solid which precipitated was collected, dried and recrystallised from ethyl acetate with hot filtering to give N-(2-methoxyethyl)-1-[1-(4-chlorophenyl)cyclobutyl]-3-methylbutylamine maleate (m.p. 131°-133° C.).

EXAMPLE 89

A solution of 1-phenyl-1-cyclobutanecarbonitrile (30 g) in ether (100 ml) was added dropwise to a stirred solution of cyclohexylmagnesium bromide [prepared from cyclohexyl bromide (62.3 g) and magnesium (9.5 g) in ether (200 ml)]. The ether was replaced with toluene, and the mixture was stirred at 90° C. for 24 hours. Sodium borohydride (7.3 g) was added as a slurry in ethanol (200 ml) and the mixture was heated under reflux for 3 hours. The cooled mixture was acidified, basified, diluted with ether and water, and filtered (Celite). The organic layer was separated and the aqueous layer was extracted with ether. The combined extracts were washed, dried and the solvent removed by evaporation to give (cyclohexyl)(1-phenylcyclobutyl)methylamine which was isolated by conversion into a hydrochloride salt.

A solution of dicyclohexylcarbodiimide (2.6 g) in dichloromethane (50 ml) was added dropwise to a stirred solution of (cyclohexyl)(1-phenylcyclobutyl)methylamine prepared from the salt isolated above and methoxyacetic acid (1.13 g) in dichloromethane (50 ml). The mixture was stirred at room temperature for 4 hours and allowed to stand at room temperature for 72 hours and filtered through diatomaceous earth (Celite). The filtrate was evaporated to remove solvent and the residue was boiled with light petroleum (b.p. 60°-80° C.) (200 ml) and filtered through diatomaceous earth (Celite). The filtrate was evaporated to leave a colourless oil which was distilled to yield N-[(cyclohexyl)(1-phenylcyclobutyl)methyl]-2-methoxyacetamide b.p. 146°-148° C. at 3.5 mm Hg.

Borane-methyl sulphide complex (2.48 ml) was added dropwise to a refluxing solution of the acetamide (2.6 g) prepared above in tetrahydrofuran (6 ml). The mixture was heated under reflux for 2 hours left at room temperature for 16 hours and heated under reflux for 2 hours, cooled in ice, and hydrolysed by the slow dropwise addition of ice-water. The mixture was acidified, basified, and extracted with ether. The washed and dried extracts were evaporated to leave an oil which was purified by high pressure liquid chromatography to give N-[(cyclohexyl)(1-phenylcyclobutyl)methyl]-2-methoxyethylamine as a pale yellow oil the physical characteristics of which were not determined.

EXAMPLE 90

A mixture of 1-[1-(3,4-dichlorophenyl)cyclobutyl]-butylamine (2 g), methyl acrylate (2 g) and toluene (10 ml) was heated under reflux with stirring for a total of 20 hours. Methyl acrylate (0.5 ml) was added, and heating under reflux and stirring were continued for 3 days. The solvent was removed in vacuo, and the oily residue as purified by chromatography on a silica column using a mixture of 9 parts petroleum ether (b.p. 40°-60°) and 1 part acetone as eluant. From the eluate methyl 3-{1-[1-(3,4-dichlorophenyl)cyclobutyl]butylamino}propanoate was obtained as a pale yellow oil, the physical properties of which were not determined.

EXAMPLE 91

A mixture of 1-[1-(3,4-dichlorophenyl)cyclobutyl]butylamine (2.0 g) and 1,2-epoxybutane (3 ml) was heated in a sealed tube at 90°–95° C. for 3 days. A further portion of the epoxide (4 ml) was added and the mixture was heated in the sealed tube for a further 3 days.

The reaction mixture was diluted with ether and treated with a solution of maleic acid in ether to give a colourless oil which crystallised to give a white solid which was recrystallised from propan-2-ol to give 1-1-[1-(3,4-dichlorophenyl)cyclobutyl]butylaminobutan-2-ol maleate (m.p. 120°–122° C.).

EXAMPLE 92

A mixture of 2-[1-(3,4-dichlorophenyl)cyclobutyl]acetic acid (1.8 g prepared in a similar manner to that described in Example 38 of British Patent Specification No. 2098602A for the corresponding 4-chloro compound) and thionyl chloride (6.5 ml) was heated under reflux for 1 hour. Excess thionyl chloride was then evaporated in vacuo and the residue was added dropwise to a stirred, ice-cooled solution of 2-methoxyethylamine (1.05 g) in dry ether (10 ml). The resulting mixture was stirred at room temperature for 45 minutes and water (20 ml) as added. The product was extracted with ether and the extracts were combined, dried and evaporated to give N-(2-methoxyethyl)-2-[1-(3,4-dichlorophenyl)cyclobutyl]acetamide as an oil.

A solution of the acetamide (2.02 g) in dry ether (18 ml) was added dropwise in an atmosphere of nitrogen to a stirred mixture of lithium aluminium hydride (0.63 g) and dry ether (9 ml). When the addition was complete the mixture was stirred at ambient temperature for 2 hours then at reflux for 3 hours. It was then cooled in ice and water (0.7 ml), 5N aqueous sodium hydroxide (0.7 ml) and water (2.1 ml) were added sequentially. The mixture was stirred for 30 minutes and was filtered and the filtrate extracted with N hydrochloric acid. The acidic extracts were washed with ether and basified and the product was extracted with ether. The extracts were washed with water, dried and evaporated to give an oil which was redissolved in ether and hydrogen chloride was bubbled into the solution to give a colourless solid. The solid was collected and suspended in boiling petroleum ether (b.p. 40°–60° C.) and then ethyl acetate was added slowly to give a clear solution. N-(2-methoxyethyl)-2-[1-(3,4-dichlorophenyl)cyclobutyl]ethylamine hydrochloride (m.p. 114.5°–116° C.) crystallised on cooling.

EXAMPLE 93

The product of Example 16 (4.0 g) was suspended in ethyl acetate (20 ml) and acetic anhydride (1.3 g) was added. The mixture was heated under reflux for 3½ hours. The solvent was removed by evaporation and residual acetic acid removed azeotropically with toluene. The residue (4.0 g) was dissolved in water (40 ml) and treated with ether (35 ml) and aqueous ammonia (4 ml). The ether layer was separated, dried and evaporated to give an oil (3.2 g) which was dissolved in ether and treated with a solution of maleic acid (1.2 g) in ether (40 ml) to give 2-{1-[1-(3,4-dichlorophenyl)cyclobutyl]ethylamino}ethyl acetate maleate.

EXAMPLE 94

Cyclohexylacetyl chloride (3.21 g) in dry ether (100 ml) was added over 30 minutes to a stirred mixture of 1-[1-(3,4-dichlorophenyl)cyclobutyl]ethylamine (4.88 g), triethylamine (2.5 g) and dry ether (100 ml) at 0°–6° C. After stirring for a further 3 hours the mixture was filtered and the residue was washed with dry ether. The filtrate and washings were combined, dried and evaporated. The residue was dissolved in tetrahydrofuran (50 ml) and the solution heated under reflux in an atmosphere of nitrogen. Borane-methyl sulphide complex (3 ml) was added from a syringe. The resulting mixture was heated under reflux for 12 hours after which it was cooled and ice-water and then 5N hydrochloric acid were added. The organic solvent was removed by evaporation and the residue was cooled, basified with 5N sodium hydroxide solution and extracted with ether. The extracts were washed with water, dried and the ether removed by evaporation. From the residue N-(2-cyclohexylethyl)-1-[1-(3,4-dichlorophenyl)cyclobutyl]ethylamine was obtained by distillation (b.p. 170° C./0.5 mm Hg).

EXAMPLE 95

2-Ethylbutylmagnesium bromide was prepared by adding a solution of 2-ethylbutyl bromide (25.1 g) in dry ether (25 ml) dropwise to a rapidly stirring mixture of magnesium turnings (3.6 g) in dry ether (100 ml) under nitrogen. When all of the magnesium had dissolved, a solution of 1-(3,4-dichlorophenyl)-1-cyclobutanecarbonitrile (23.6 g) in dry ether (50 ml) was added. The ether was gradually replaced by dry toluene (200 ml) and the mixture stirred and heated at 110° C. for 1 hour.

A solution of sodium borohydride (6 g) in ethanol (300 ml) was added and the mixture heated under reflux for 4 hours. After cooling the mixture, water and 5N hydrochloric acid were added. The mixture was basified and the organic solvents removed by evaporation. The residual aqueous layer was basified and extracted into ether. The extract was washed, dried and evaporated to give a residue which was distilled at 146°–150° C./0.1 mm Hg. 1-[1-(3,4-Dichlorophenyl)cyclobutyl]-3-ethylpentylamine maleate was made by adding a solution of excess maleic acid in ether to a solution of the distilled amine in ether and collecting the white solid.

A solution of dry triethylamine (10.1 g) in dry ether (20 ml) was added dropwise to a stirred mixture of the maleate (18.0 g) prepared as described above in dry ether (100 ml). A solution of methoxyacetylchloride (4.89 g) in dry ether (10 ml) was added dropwise keeping the temperature in the range 5°–10° C. The mixture was stirred at room temperature for two hours and then filtered. The filtrate was diluted with water. The ethereal layer was washed with 5N hydrochloric acid, water, dried and the solvent removed by evaporation to give an oil which was purified by chromatography on a florisil column eluted with a 1:1 mixture of ether and petroleum ether (b.p. 40°–60° C.). N-{1-[1-(3,4-Dichlorophenyl)cyclobutyl]-3-ethylpentyl}-2-methoxyacetamide (m.p. 72°–74° C.) was obtained on standing from the largest of the fractions from the column.

Borane-methyl sulphide complex (2 ml) was added dropwise to a solution of the methoxyacetamide (5 g) prepared as described above in dry tetrahydrofuran (20 ml) at 0°–5° C. This mixture was left at ambient temperature for 7 days, then poured onto ice-water basified and extracted into ether, washed with water, dried and evaporated to dryness to give an oil. This oil was treated as above with more borane-methyl sulphide to give N-(2-methoxyethyl)-1-[1-(3,4-dichlorophenyl)cyclobutyl]-3-ethyl pentylamine (b.p. 189°–190° C./1.5 mm Hg) as an oil.

EXAMPLE 96

Acetic anhydride (5 ml) and water (5 ml) were added to the product of Example 8 in the form of its free base (1.5 g) and the mixture maintained at 30° C. for 2 hours. The mixture was stirred at ambient temperature for 16 hours and then heated to 95° C. for 16 hours. The mixture was cooled and poured into ice/water (150 ml). Aqueous sodium hydroxide solution was added and the aqueous solution extracted with ether. The extract was washed, dried and evaporated to give a residue which was triturated with ice-cold petroleum ether (b.p. 60°–80° C.) and recrystallised from petroleum ether (b.p. 80°–100° C.) to give N-acetyl-N-(2-morpholinoethyl)-1-[1-(3,4-dichlorophenyl)cyclobutyl]ethylamine (m.p. 121°–122° C.) as a white solid.

Borane-methyl sulphide complex (4 ml) was added under a nitrogen atmosphere to a solution of the amide prepared as above (0.63 g) in dry tetrahydrofuran (50 ml). The mixture was stirred for 16 hours. The residue as cooled to 0° C. and water (30 ml) added and then 2.5N sodium hydroxide solution (30 ml) added. The basic mixture was extracted with ether and the extract was washed, dried filtered and evaporated to give an oil which was dissolved in ether and the solution filtered. Passing hydrogen chloride gas through the solution gave N-ethyl-N-(2-morpholino-ethyl)-1-[1-(3,4-dichlorophenyl)cyclobutyl]ethylamine dihydrochloride hydrate (m.p. 105°–115° C.).

EXAMPLE 97

In a similar manner to that described in Example 96 N-ethyl-N-(2-methoxyethyl)-1-[1-(3,4-dichlorophenyl)cyclobutyl]ethylamine hydrochloride hydrate (m.p. 115°–124° C.) was prepared from the product of Example 17.

EXAMPLE 98

In a similar manner to that described in Example 96, N-(2-morpholinoethyl)-N-propyl-1-[1-(3,4-dichlorophenyl)cyclobutyl]ethylamine dihydrochloride (2.23 g) hydrate (m.p. 105°–115° C.) was prepared by the reaction of the product of Example 8 with propionic anhydride followed by reduction of the resulting N-propionyl compound.

EXAMPLE 99

A solution of 2-thienyl bromide (24.5 g) in dry ether (20 ml) was added to a rapidly stirred mixture of magnesium turnings (3.6 g) in dry ether (25 ml). When the magnesium had totally dissolved a solution of 1-(4-chlorophenyl)-1-cyclobutanecarbonitrile (20.2 g) in dry ether (50 ml) was added and the mixture heated under reflux with stirring for 3 hours. A solid precipitated which was separated and dissolved in ethanol (50 ml). A suspension of sodium borohydride (7 g) in ethanol (100 ml) was added and the mixture heated under reflux for 2 hours. 5N Hydrochloric acid was added to the cooled reaction mixture which was basified and extracted with ether. The ether was removed by evaporation and the residue dissolved in ether. Passing hydrogen chloride gas through the dried solution gave [1-(4-chlorophenyl)cyclobutyl](thien-2-yl)methylamine hydrochloride.

4-Pyridinecarboxaldehyde (0.6 g) was added to the product obtained above in the form of its free base (1.4 g) at 110°–115° C. The mixture was stirred and heated at 135°–140° C. for 30 minutes. After the mixture had been cooled to room temperature a solution of sodium borohydride (1 g) in ethanol (50 ml) was added and the mixture heated under reflux for two hours. After cooling excess 5N hydrochloric acid was added and the reaction mixture made basic by adding 5N aqueous sodium hydroxide solution. The ethanol was removed by evaporation and the mixture extracted with ether. The ether extract was washed with water and dried. Hydrogen chloride gas was passed through the ethereal solution which was then evaporated to dryness. Trituration of the residue with propan-2-ol gave N-(4-pyridylmethyl)-[1-(4-chlorophenyl)cyclobutyl](2-thienyl)methylamine dihydrochloride (m.p. 226°–230° C.).

EXAMPLE 100 n-Butyllithium (160 ml of a 1.55M solution in hexane) was added dropwise under a nitrogen atmosphere to a cold (0° C.) stirred solution of 1-methylimidazole (20 g) in ether (1000 ml) and the mixture was stirred at 0° C. for 1 hour. A solution of 1-(3,4-dichlorophenyl)-1-cyclobutanecarbonitrile (50 g) in ether (200 ml) was added dropwise at 0° C. and the mixture was stirred at 0° C. for 2 hours before being cooled to −40° C. Methanol (50 ml) in ether (100 ml) was added at −40° C. to −30° C., then water (100 ml) was added at −30° C., the mixture was allowed to warm to −10° C. and a further portion of water (100 ml) was added.

The aqueous layer was extracted with ether and the dried ethereal extracts were added in portions to a hot mixture of sodium borohydride (20 g) and ethanol (500 ml). The ether was evaporated and the mixture heated under reflux for 16 hours and evaporated in vacuo. The residue was diluted with water (500 ml), acidified with dilute aqueous hydrochloric acid, basified with dilute aqueous sodium hydroxide, and extracted with ether. The extracts were washed and dried and the solvent removed by evaporation to leave an orange oil which crystallised from petroleum ether (b.p. 40°–60° C.) to give pale yellow microplates.

The solid was rereduced with sodium borohydride in boiling propan-2-ol to give [1-(3,4-dichlorophenyl)cyclobutyl][2-(1-methylimidazolyl)]methylamine as a viscous yellow oil.

Methoxyacetyl chloride (1.2 g) was added dropwise to a solution of the base prepared as above (3 g) and triethylamine (1.5 g) in ether (50 ml) and the mixture was heated under reflux for two hours and allowed to stand at ambient temperature for sixteen hours. The reaction mixture was poured into water and the resulting mixture was extracted with ether. The ether extracts were washed with water, dried and the ether removed to yield N-{[1-(3,4-dichlorophenyl)cyclobutyl][1-methylimidazol-2-yl]methyl}-2-methoxyacetamide.

Borane-methyl sulphide complex (5 ml) was added dropwise to a solution of the acetamide (3.3 g) prepared as above in tetrahydrofuran (100 ml) and the mixture stirred for 2 days. Ice-water was added cautiously and the resulting mixture basified. The basified mixture was extracted with ether and the extracts washed and dried. Removal of the ether gave a residue which was dissolved in ether. Hydrogen chloride gas was passed through the solution to give a hydrochloride of N-{[1-(3,4-dichlorophenyl)cyclobutyl][1-methylimidazol-2-yl]methyl}-2-methoxyethylamine containing 1.8 moles of hydrochloride and 1.6 moles of water which decomposed when heated to 150° C.

EXAMPLE 101

A mixture of the base prepared as described in Example 100 (3 g) and 4-vinylpyridine (1.5 g) was heated at 100° C. for 3 days under nitrogen. After standing for 3 days at ambient temperature the reaction mixture as heated under reflux with a mixture of ether (150 ml) and ethyl acetate (150 ml) and filtered hot. The filtrate yielded a brown oil which was dissolved in hot ether and filtered. Hydrogen chloride gas was passed through the cooled solution to give a solid which was basified and purified by column chromatography and recrystallisation from a mixture of ether and petroleum ether (b.p. 40°-60° C.) to yield N-{[1-(3,4-dichlorophenyl)cyclobutyl][1-methylimidazol-2-yl]methyl}-2-(4-pyridyl)ethylamine hydrate (m.p. 110°-111° C.).

EXAMPLE 102 TO 104

The compound of Example 8 in the form of its free base was converted into the following salts

| Example | Salt | m.p. | Notes |
|---------|------|------|-------|
| 102 | dimaleate | 160–163° | |
| 103 | dicitrate | 65–75° | (0.66)hydrate |
| 104 | (1.3)tartrate | 180–190° | |

EXAMPLE 105

Pharmaceutical compositions containing any one of the compounds of formula I disclosed in Examples 1 to 104 are prepared in the following manner.

EXAMPLE 105(a)

Tablets are prepared from the following ingredients:

| | Parts by Weight |
|---|---|
| Active Ingredient | 50.0 |
| Lactose | 78.5 |
| Polyvinylpyrrolidone | 5.0 |
| Maize Starch | 15.0 |
| Magnesium Stearate | 1.5 |

The active ingredient, the lactose and some of the starch are mixed and granulated with a solution of the polyvinylpyrrolidone in ethanol. The granulate is mixed with the stearic acid and the rest of the starch and the mixture is compressed in a tabletting machine to give tablets containing 50.0 mg of the active ingredient.

EXAMPLE 105(b)

Capsules are prepared in the following way. A mixture of the active ingredient (45 parts by weight) and lactose powder (205 parts by weight) is filled into hard gelatin capsules, each capsule containing 45 mg of the active ingredient.

EXAMPLE 105(c)

In the preparation of enteric coated tablets, the tablets described in Example 105(a) are given a thin coat of shellac varnish, followed by 20 coats of cellulose acetate phthalate in a manner well known in the art. In a similar manner the capsules of Example 105(b) may be provided with an enteric coating.

EXAMPLE 105(d)

Vials containing a solution of water-soluble compounds of the present invention suitable for injection are prepared from the following ingredients:

| Active Ingredient | 1100 g |
|---|---|
| Mannitol | 1100 g |
| Water, freshly distilled | to 11 liters |

The active ingredient and mannitol are dissolved in some of the water and the volume of the solution is adjusted to 11 liters. The resulting solution is sterilised by filtration and filled into sterile vials each containing 1.65 ml of solution.

We claim:

1. A compound of the Formula I:

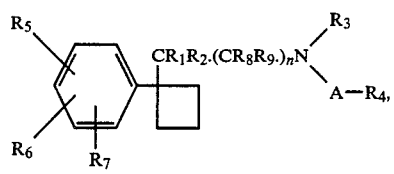

a pharmaceutically acceptable salt thereof or a hydrate of a pharmaceutically acceptable salt in which n=0 or 1;

when n=0, $R_1$ is H, straight or branched chain alkyl of 1 to 6 carbon atoms, cycloalkyl of 3 to 7 carbon atoms, cycloalkylmethyl in which the cycloalkyl group contains 3 to 7 carbon atoms, alkenyl of 3 to 6 carbon atoms, alkynyl of 3 to 6 carbon atoms, a heterocyclic ring selected from the group consisting of furyl, thienyl, pyrrolyl, pyridyl, tetrahydrofuryl, tetrahydrothienyl, imidazolyl, pyrazolyl, pyrazinyl, pyrimidinyl, pyridazinyl, triazolyl, tetrazolyl, dithianyl and thiazolyl, said heterocyclic ring being unsubstituted or substituted by one or more alkyl groups of 1 to 3 carbon atoms, one or more halo groups, one or more alkoxy groups of 1 to 3 carbon atoms or one or more trifluoromethyl groups, or a group of the Formula II:

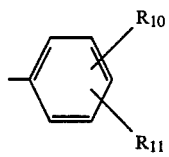

when n=1, $R_1$ is H or alkyl of 1 to 3 carbon atoms;
$R_2$ is H or alkyl of 1 to 3 carbon atoms;
$R_2$ is H or alkyl of 1 to 3 carbon atoms;
$R_3$ is H or straight or branched chain alkyl of 1 to 4 carbon atoms;
A is a group of the Formula III:

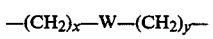

in which W is an oxygen atom or a group of the Formula $-S(O)_m-$ in which m is 0, 1 or 2, a group of the Formula $-CR_{12}R_{13}-$, cycloalkylidene of 3 to 6 carbon atoms or a cycloalkylene of 3 to 6 carbon atoms; x is 0 or an integer from 1 to 5; y is 0 or an integer from 1 to 5 with the proviso that when W is an oxygen atom or a group of the Formula $S(O)_m$, x and y are both integers from 1 to 5; $R_{12}$ and $R_{13}$ are the same or different and each is H, alkyl of 1 to 3 carbon atoms, hydroxy, methoxy or benzyl;

$R_4$ is phenyl unsubstituted or substituted by one or more halo, hydroxy, alkoxy of 1 to 3 carbon atoms or alkyl of 1 to 3 carbon atoms, a heterocyclic ring selected from the group consisting of furyl, thienyl, pyrrolyl, pyridyl, tetrahydrofuryl, tetrahydrothienyl, pyrrolinyl, piperidyl, imidazolyl, pyrazolyl, pyrazinyl, pyrimidinyl, pyridazinyl, imidazolidinyl, imidazolinyl, pyrazolidinyl, pyrazolinyl, triazolyl, tetrazolyl, thiazolyl, isoxazolyl, morpholinyl, thiomorpholinyl, tetrahydro and dihydro derivatives of thiazolyl or isoxazolyl, cyano, carbamoyl of the Formula —$CONR_{14}R_{15}$ in which $R_{14}$ and $R_{15}$ are the same or different and each is H or alkyl of 1 to 3 carbon atoms or $R_{14}$ and $R_{15}$ together with the nitrogen atom to which they are attached form a heterocyclic ring of 4- to 6-ring members, alkoxycarbonyl of the Formula —$COOR_{16}$ in which $R_{16}$ is alkyl of 1 to 3 carbon atoms, amido of the Formula —$N(R_{17})COR_{18}$ in which $R_{17}$ and $R_{18}$ are the same or different and each is alkyl of 1 to 4 carbon atoms or $R_{17}$ and $R_{18}$ together with the nitrogen atom and carbonyl group to which they are attached form a 5- or 6-member heterocyclic ring, acyloxy of the Formula —$OCOR_{19}$— in which $R_{19}$ is alkyl of 1 to 3 carbon atoms, thiol, or a group of the Formula —$OR_{20}$, —$SR_{20}$, —$SOR_{20}$ or $SO_2R_{20}$ in which $R_{20}$ is straight or branched chain alkyl of 1 to 4 carbon atoms or phenyl unsubstituted or substituted by halo, hydroxy, alkoxy or 1 to 3 carbon atoms or alkyl of 1 to 3 carbon atoms;

$R_5$, $R_6$ and $R_7$ are the same or different and each is H, halo, trifluoromethyl, hydroxy, alkyl of 1 to 3 carbon atoms, alkoxy of 1 to 3 carbon atoms or alkylthio of 1 to 3 carbon atoms, or phenyl or $R_5$ and $R_6$, together with the carbon atoms to which they are attached, form a second benzene ring which is unsubstituted or substituted by halo, alkyl or 1 to 3 carbon atoms, or alkoxy of 1 to 3 carbon atoms, or the substituents on the second benzene ring together with the carbon atoms to which they are attached form a further benzene ring;

$R_8$ and $R_9$ are the same or different and each is H or alkyl of 1 to 3 carbon atoms; and $R_{10}$ and $R_{11}$ are the same or different and each is H, halo, alkyl of 1 to 3 carbon atoms or alkoxy of 1 to 3 carbon atoms.

2. A compound according to claim 1 wherein $R_1$ is methyl, ethyl, propyl, isopropyl, isobutyl, branched hexyl, cyclopropyl, cyclobutyl, cyclopentyl, cyclohexyl, cyclopropylmethyl, cyclobutylmethyl, cyclopentylmethyl, cyclohexylmethyl, allyl or propynyl.

3. A compound according to claim 1 wherein $R_3$ is methyl, ethyl, or propyl.

4. A compound according to claim 1 wherein W is a group of the Formula —$CR_{12}R_{13}$— wherein $R_{12}$ is methyl, ethyl, or propyl and $R_{13}$ is H or methyl.

5. A compound according to claim 1 wherein $R_5$, $R_6$ and $R_7$ are the same or different and each is selected from the group consisting of H, fluoro, chloro, bromo, iodo, methyl, methoxy and methylthio.

6. A compound according to claim 1 wherein $R_5$ and $R_6$ together with the carbon atoms to which they are attached form a second benzene ring unsubstituted or substituted by one or more halo groups, one or more alkyl groups of 1 to 3 carbon atoms or one or more alkoxy groups of 1 to 3 carbon atoms or the substituents on the second benzene ring together with the carbon atoms to which they are attached form a further benzene ring.

7. A compound according to claim 6 wherein the substituents on the second benzene ring are fluoro, chloro, bromo, methyl or methoxy.

8. A compound according to claim 5 wherein $R_5$ is methyl, methylthio or phenyl and $R_6$ is H or halo or $R_5$ and $R_6$ together with the carbon atom to which they are attached form a second benzene ring.

9. A compound according to claim 1 in the form of the hydrochloride, maleate, acetate, citrate, fumarate, tartrate, succinate, aspartate or glutamate salt.

10. A compound according to claim 1 wherein A is alkylene of 1 to 3 carbon atoms and $R_4$ is selected from the group consisting of hydroxy and —$OR_{20}$ in which $R_{20}$ is methyl, ethyl, propyl, isopropyl, butyl or isobutyl.

11. A compound according to claim 1 wherein $R_1$ is methyl or propyl, A is alkylene of 2 carbon atoms and $R_4$ is morpholino.

12. The compound according to claim 1 which is N-(2-morpholinoethyl)-1-(1-phenylcyclobutyl)ethylamine or a pharmaceutically acceptable salt thereof.

13. The compound according to claim 1 which is N-(2-morpholinoethyl)-1-[1-(4-biphenyl)cyclobutyl]-ethylamine or a pharmaceutically acceptable salt thereof.

14. A pharmaceutical composition useful for treating depression in humans which comprises a therapeutically effective amount of a compound of the Formula I:

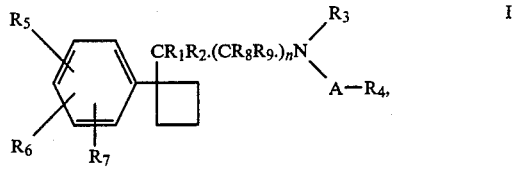

a pharmaceutically acceptable salt thereof or a hydrate of a pharmaceutically acceptable salt in which n=0 or 1;

when n=0, $R_1$ is H, straight or branched chain alkyl of 1 to 6 carbon atoms, cycloalkyl of 3 to 7 carbon atoms, cycloalkylmethyl in which the cycloalkyl group contains 3 to 7 carbon atoms, alkenyl of 3 to 6 carbon atoms, alkynyl of 3 to 6 carbon atoms, a heterocyclic ring selected from the group consisting of furyl, thienyl, pyrrolyl, pyridyl, tetrahydrofuryl, tetrahydrothienyl, imidazolyl, pyrazolyl, pyrazinyl, pyrimidinyl, pyridazinyl, triazolyl, tetrazolyl, dithianyl and thiazolyl, said heterocyclic ring being unsubstituted or substituted by one or more alkyl groups of 1 to 3 carbon atoms, one or more halo groups, one or more alkoxy groups of 1 to 3 carbon atoms or one or more trifluoromethyl groups, or a group of the Formula II:

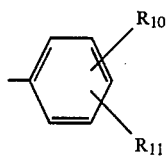

when n=1, $R_1$ is H or alkyl of 1 to 3 carbon atoms;
$R_2$ is H or alkyl of 1 to 3 carbon atoms;
$R_2$ is H or alkyl of 1 to 3 carbon atoms;
$R_3$ is H or straight or branched chain alkyl of 1 to 4 carbon atoms;
A is a group of the Formula III:

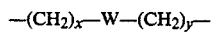

in which W is an oxygen atom or a group of the Formula $-S(O)_m-$ in which m is 0, 1 or 2, a group of the Formula $-CR_{12}R_{13}-$, cycloalkylidene of 3 to 6 carbon atoms or a cycloalkylene of 3 to 6 carbon atoms; x is 0 or an integer from 1 to 5; y is 0 or an integer from 1 to 5 with the proviso that when W is an oxygen atom or a group of the Formula $S(O)_m$, x and y are both integers from 1 to 5; $R_{12}$ and $R_{13}$ are the same or different and each is H, alkyl of 1 to 3 carbon atoms, hydroxy, methoxy or benzyl;
$R_4$ is phenyl unsubstituted or substituted by one or more halo, hydroxy, alkoxy of 1 to 3 carbon atoms or alkyl of 1 to 3 carbon atoms, a heterocyclic ring selected from the group consisting of furyl, thienyl, pyrrolyl, pyridyl, tetrahydrofuryl, tetrahydrothienyl, pyrrolinyl, piperidyl, imidazolyl, pyrazolyl, pyrazinyl, pyrimidinyl, pyridazinyl, imidazolidinyl, imidazolinyl, pyrazolidinyl, pyrazolinyl, triazolyl, tetrazolyl, thiazolyl, isoxazolyl, morpholinyl, thiomorpholinyl, tetrahydro and dihydro derivatives of thiazolyl or isoxazolyl, cyano, carbamoyl of the Formula $-CONR_{14}R_{15}$ in which $R_{14}$ and $R_{15}$ are the same or different and each is H or aklyl of 1 to 3 carbon atoms or $R_{14}$ and $R_{15}$ together with the nitrogen atom to which they are attached form a heterocyclic ring of 4- to 6-ring members, alkoxycarbonyl of the Formula $-COOR_{16}$ in which $R_{16}$ is alkyl of 1 to 3 carbon atoms, amido of the Formula $-N(R_{17})COR_{18}$ in which $R_{17}$ and $R_{18}$ are the same or different and each is alkyl of 1 to 4 carbon atoms or $R_{17}$ and $R_{18}$ together with the nitrogen atom and carbonyl group to which they are attached form a 5- or 6-member heterocyclic ring, acyloxy of the Formula $-OCOR_{19}-$ in which $R_{19}$ is alkyl of 1 to 3 carbon atoms, thiol, or a group of the Formula $-OR_{20}$, $-SR_{20}$, $-SOR_{20}$ or $SO_2R_{20}$ in which $R_{20}$ is straight or branched chain alkyl of 1 to 4 carbon atoms or phenyl unsubstituted or substituted by halo, hydroxy, alkoxy or 1 to 3 carbon atoms or alkyl of 1 to 3 carbon atoms;
$R_5$, $R_6$ and $R_7$ are the same or different and each is H, halo, trifluoromethyl, hydroxy, alkyl of 1 to 3 carbon atoms, alkoxy of 1 to 3 carbon atoms or alkylthio of 1 to 3 carbon atoms, or phenyl or $R_5$ and $R_6$, together with the carbon atoms to which they are attached, form a second benzene ring which is unsubstituted or substituted by halo, alkyl or 1 to 3 carbon atoms, or alkoxy of 1 to 3 carbon atoms, or the substituents on the second benzene ring together with the carbon atoms to which they are attached form a further benzene ring;
$R_8$ and $R_9$ are the same or different and each is H or alkyl of 1 to 3 carbon atoms;
and $R_{10}$ and $R_{11}$ are the same or different and each is H, halo, alkyl of 1 to 3 carbon atoms or alkoxy of 1 to 3 carbon atoms; in combination with a pharmaceutically acceptable carrier.

15. A composition according to claim 14 wherein $R_1$ is methyl, ethyl, propyl, isopropyl, isobutyl, branched hexyl, cyclopropyl, cyclobutyl, cyclopentyl, cyclohexyl, cyclopropylmethyl, cyclobutylmethyl, cyclopentylmethyl, cyclohexylmethyl, allyl or propynyl.

16. A composition according to claim 14 wherein $R_3$ is methyl, ethyl, or propyl.

17. A composition according to claim 14 wherein W is a group of the Formula $-CR_{12}R_{13}-$ in which $R_{12}$ is methyl, ethyl, or propyl and $R_{13}$ is H or methyl.

18. A composition according to claim 14 wherein $R_5$, $R_6$ and $R_7$ are the same or different and each is selected from the group consisting of H, fluoro, chloro, bromo, iodo, methyl, methoxy and methylthio.

19. A composition according to claim 14 wherein $R_5$ and $R_6$ together with the carbon atoms to which they are attached form a second benzene ring unsubstituted or substituted by one or more halo groups, one or more alkyl groups of 1 to 3 carbon atoms or one or more alkoxy groups of 1 to 3 carbon atoms or the substituents on the second benzene ring together with the carbon atoms to which they are attached form a further benzene ring.

20. A composition according to claim 14 wherein the substituents on the second benzene ring are fluoro, chloro, bromo, methyl or methoxy.

21. A composition according to claim 14 wherein $R_5$ is methyl, methylthio or phenyl and $R_6$ is H or halo or $R_5$ and $R_6$ together with the carbon atom to which they are attached form a second benzene ring.

22. A composition according to claim 14 wherein the compound is in the form of the hydrochloride, maleate, acetate, citrate, fumarate, tartrate, succinate, aspartate or glutamate salt.

23. A composition according to claim 14 wherein A is alkylene of 1 to 3 carbon atoms and $R_4$ is selected from the group consisting of hydroxy and $-OR_{20}$ in which $R_{20}$ is methyl, ethyl, propyl, isopropyl, butyl or isobutyl.

24. A composition according to claim 14 wherein $R_1$ is methyl or propyl, A is alkylene of 2 carbon atoms and $R_4$ is morpholino.

25. A composition according to claim 14 wherein the compound is N-(2-morpholinoethyl)-1-(1-phenylcyclobutyl)ethylamine or a pharmaceutically acceptable salt thereof.

26. A composition according to claim 14 wherein the compound is N-(2-morpholinoethyl)-1-[1-(4-biphenyl)-cyclobutyl]-ethylamine.

27. A composition according to claim 14 in unit dosage form.

28. A method of treating depression in humans which comprises administering to a human in need thereof a therapeutically effective amount of a compound of the Formula I:

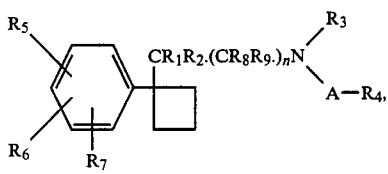

a pharmaceutically acceptable salt thereof or a hydrate of a pharmaceutically acceptable salt in which n=0 or 1;

when n=0, $R_1$ is H, straight or branched chain alkyl of 1 to 6 carbon atoms, cycloalkyl of 3 to 7 carbon atoms, cycloalkylmethyl in which the cycloalkyl group contains 3 to 7 carbon atoms, alkenyl of 3 to 6 carbon atoms, alkynyl of 3 to 6 carbon atoms, a heterocyclic ring selected from the group consisting of furyl, thienyl, pyrrolyl, pyridyl, tetrahydrofuryl, tetrahydrothienyl, imidazolyl, pyrazolyl, pyrazinyl, pyrimidinyl, pyridazinyl, triazolyl, tetrazolyl, dithianyl and thiazolyl, said heterocyclic ring being unsubstituted or substituted by one or more alkyl groups of 1 to 3 carbon atoms, one or more halo groups, one or more alkoxy groups of 1 to 3 carbon atoms or one or more trifluoromethyl groups, or a group of the Formula II:

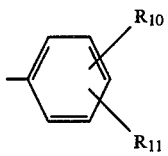

when n=1, $R_1$ is H or alkyl of 1 to 3 carbon atoms;
$R_2$ is H or alkyl of 1 to 3 carbon atoms;
$R_2$ is H or alkyl 1 to 3 carbon atoms;
$R_3$ is H or straight or branched chain alkyl of 1 to 4 carbon atoms;
A is a group of the Formula III:

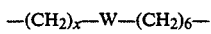

in which W is an oxygen atom or a group of the Formula —S(O)$_m$— in which m is 0, 1 or 2, a group of the Formula —CR$_{12}$R$_{13}$—, cycloalkylidene of 3 to 6 carbon atoms or a cycloalkylene of 3 to 6 carbon atoms; x is 0 or an integer from 1 to 5; y is 0 or an integer from 1 to 5 with the proviso that when W is an oxygen atom or a group of the Formula S(O)$_m$, x and y are both integers from 1 to 5; $R_{12}$ and $R_{13}$ are the same or different and each is H, alkyl of 1 to 3 carbon atoms, hydroxy, methoxy or benzyl;

$R_4$ is phenyl unsubstituted or substituted by one or more halo, hydroxy, alkoxy of 1 to 3 carbon atoms or alkyl of 1 to 3 carbon atoms, a heterocyclic ring selected from the group consisting of furyl, thienyl, pyrrolyl, pyridyl, tetrahydrofuryl, tetrahydrothienyl, pyrrolinyl, piperidyl, imidazolyl, pyrazolyl, pyrazinyl, pyrimidinyl, pyridazinyl, imidazolidinyl, imidazolinyl, pyrazolidinyl, pyrazolinyl, triazolyl, tetrazolyl, thiazolyl, isoxazolyl, morpholinyl, thiomorpholinyl, tetrahydro and dihydro derivatives of thiazolyl or isoxazolyl, cyano, carbamoyl of the Formula —CONR$_{14}$R$_{15}$ in which $R_{14}$ and $R_{15}$ are the same or different and each is H or aklyl of 1 to 3 carbon atoms or $R_{14}$ and $R_{15}$ together with the nitrogen atom to which they are attached form a heterocyclic ring of 4- to 6-ring members, alkoxycarbonyl of the Formula —COOR$_{16}$ in which $R_{16}$ is alkyl of 1 to 3 carbon atoms, amido of the Formula —N(R$_{17}$)COR$_{18}$ in which $R_{17}$ and $R_{18}$ are the same or different and each is alkyl of 1 to 4 carbon atoms or $R_{17}$ and $R_{18}$ together with the nitrogen atom and carbonyl group to which they are attached form a 5- or 6-member heterocyclic ring, acyloxy of the Formula —OCOR$_{19}$— in which $R_{19}$ is alkyl of 1 to 3 carbon atoms, thiol, or a group of the Formula —OR$_{20}$, —SR$_{20}$, —SOR$_{20}$ or SO$_2$R$_{20}$ in which $R_{20}$ is straight or branched chain alkyl of 1 to 4 carbon atoms or phenyl unsubstituted or substituted by halo, hydroxy, alkoxy or 1 to 3 carbon atoms or alkyl of 1 to 3 carbon atoms;

$R_5$, $R_6$ and $R_7$ are the same or different and each is H, halo, trifluoromethyl, hydroxy, alkyl of 1 to 3 carbon atoms, alkoxy of 1 to 3 carbon atoms or alkylthio of 1 to 3 carbon atoms, or phenyl or $R_5$ and $R_6$, together with the carbon atoms to which they are attached, form a second benzene ring which is unsubstituted or substituted by halo, alkyl or 1 to 3 carbon atoms, or alkoxy of 1 to 3 carbon atoms, or the substituents on the second benzene ring together with the carbon atoms to which they are attached form a further benzene ring;

$R_8$ and $R_9$ are the same or different and each is H or alkyl of 1 to 3 carbon atoms;

and $R_{10}$ and $R_{11}$ are the same or different and each is H, halo, alkyl of 1 to 3 carbon atoms or alkoxy of 1 to 3 carbon atoms; in combination with a pharmaceutically acceptable carrier.

29. A method according to claim 28 wherein $R_1$ is methyl, ethyl, propyl, isopropyl, isobutyl, branched hexyl, cyclopropyl, cyclobutyl, cyclopentyl, cyclohexyl, cyclopropylmethyl, cyclobutylmethyl, cyclopentylmethyl, cyclohexylmethyl, allyl or propynyl.

30. A method according to claim 28 wherein $R_3$ is methyl, ethyl, or propyl.

31. A method according to claim 28 wherein W is a group of the Formula —CR$_{12}$R$_{13}$— in which $R_{12}$ is methyl, ethyl, or propyl and $R_{13}$ is H or methyl.

32. A method according to claim 28 wherein $R_5$, $R_6$ and $R_7$ are the same or different and each is selected from the group consisting of H, fluoro, chloro, bromo, iodo, methyl, methoxy and methylthio.

33. A method according to claim 28 wherein $R_5$ and $R_6$ together with the carbon atoms to which they are attached form a second benzene ring unsubstituted or substituted by one or more halo groups, one or more alkyl groups of 1 to 3 carbon atoms or one or more alkoxy groups of 1 to 3 carbon atoms or the substituents on the second benzene ring together with the carbon atoms to which they are attached form a further benzene ring.

34. A method according to claim 28 wherein the substituents on the second benzene ring are fluoro, chloro, bromo, methyl or methoxy.

35. A method according to claim 28 wherein $R_5$ is methyl, methylthio or phenyl and $R_6$ is H or halo or $R_5$ and $R_6$ together with the carbon atom to which they are attached form a second benzene ring.

36. A method according to claim 28 wherein the compound is in the form of the hydrochloride, maleate, acetate, citrate, fumarate, tartrate, succinate, aspartate or glutamate salt.

37. A method according to claim 28 wherein A is alkylene of 1 to 3 carbon atoms and $R_4$ is selected from the group consisting of hydroxy and $-OR_{20}$ in which $R_{20}$ is methyl, ethyl, propyl, isopropyl, butyl or isobutyl.

38. A method according to claim 28 wherein $R_1$ is methyl or porpyl, A is alkylene of 2 carbon atoms and $R_4$ is morpholino.

39. A method according to claim 28 wherein the compound is N-(2-morpholinoethyl)-1-(1phenylcyclobutyl)ethylamine or a pharmaceutically acceptable salt thereof.

40. A method according to claim 28 wherein the compound is N-(2-morpholinoethyl)-1-[1-(4-biphenyl)-cyclobutyl]ethylamine.

* * * * *

UNITED STATES PATENT AND TRADEMARK OFFICE
CERTIFICATE OF CORRECTION

PATENT NO. : 4,629,727
DATED : December 16, 1986
INVENTOR(S) : KOZLIK ET AL

It is certified that error appears in the above-identified patent and that said Letters Patent are hereby corrected as shown below:

Kindly correct the claims in the above patent to read as follows:

Claim 1, delete the third line below the structural formula II.
Claim 14, delete the third line below the structural formula II.
Claim 28, delete the third line below the structural formula II.

Claim 26, insert after "ethylamine" --or a pharmaceutically acceptable salt thereof--.

Claim 40, insert after "ethylamine" --or a pharmaceutically acceptable salt thereof--.

Glaim 38, line 2, change "porpyl" to --propyl--.

Signed and Sealed this

Fifteenth Day of March, 1988

Attest:

DONALD J. QUIGG

Attesting Officer

Commissioner of Patents and Trademarks